US006645766B2

(12) United States Patent
Luo et al.

(10) Patent No.: US 6,645,766 B2
(45) **Date of Patent: *Nov. 11, 2003**

(54) SHUTTLE VECTORS

(75) Inventors: Ying Luo, Los Altos, CA (US); Pei Wen Yu, Burlingame, CA (US); James Lorens, Portola Valley, CA (US)

(73) Assignee: Rigel Pharmaceuticals, Inc., San Francisco, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 10/043,074

(22) Filed: Jan. 7, 2002

(65) Prior Publication Data

US 2003/0017601 A1 Jan. 23, 2003

Related U.S. Application Data

(63) Continuation of application No. 09/208,827, filed on Dec. 9, 1998, now Pat. No. 6,391,582, and a continuation of application No. 09/133,944, filed on Aug. 14, 1998, now Pat. No. 6,280,937.

(51) Int. Cl.[7] ................................................ C12N 15/64

(52) U.S. Cl. ....................... 435/466; 435/477; 435/483; 435/320.1; 435/254.21

(58) Field of Search ................................ 435/69.1, 466, 435/477, 483, 320.1, 91.1, 6, 254.21

(56) References Cited

U.S. PATENT DOCUMENTS 4,783,412 A 11/1988 Bell ........................... 435/325
5,741,486 A 4/1998 Pathak et al. ............ 424/93.21
5,962,320 A 10/1999 Robinson .................... 435/366
6,391,582 B2 * 5/2002 Luo et al. .................. 435/69.1

OTHER PUBLICATIONS

Camonis et al. "Of mice and yeast: versatile vectors which permit gene expression in both budding yeast and higher eukaryotic cells" *Gene* 86(2):263–268 (1990).

Storck et al. "Rapid construction in yeast of complex targeting vectors for gene manipulation in the mouse" Nucleic Acids Research 24(22):4594–4596 (1996).

* cited by examiner

*Primary Examiner*—James Ketter
(74) *Attorney, Agent, or Firm*—Lahive & Cockfield LLP; DeAnn F. Smith, Esq.; Megan E. Williams, Esq.

(57) ABSTRACT

The invention provides shuttle vectors, and methods of using shuttle vectors, capable of expression in, at least, a mammalian cell. Furthermore, the shuttle vectors are capable of replication in at least yeast, and optionally, bacterial cells. Also provided is a method wherein yeast are transformed with a shuttle vector as provided herein. Heterologous nucleic acids flanked by 5' and 3' ends identical to a homologous recombination site within the shuttle vector are introduced to the transformed yeast and allowed to homologously recombine with the shuttle vector such that they are inserted into the vector by the yeast organism. The shuttle vector is then recovered and transferred to a mammalian cell for expression.

4 Claims, 15 Drawing Sheets

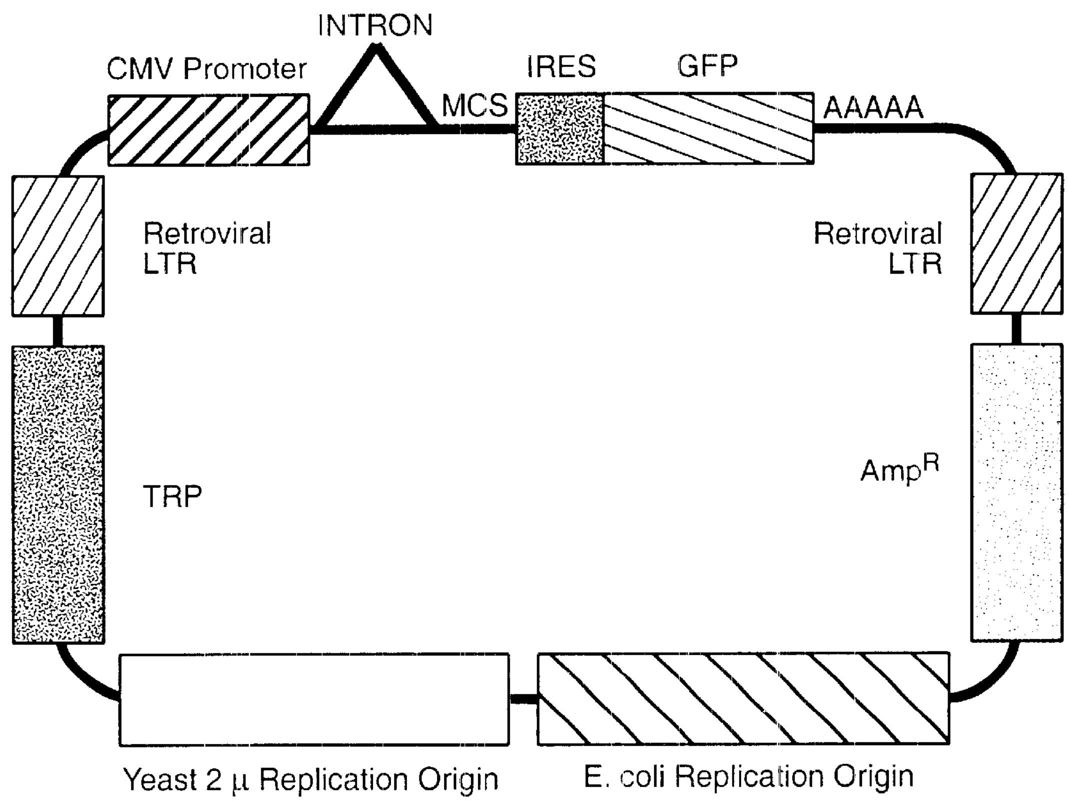
FIG._1
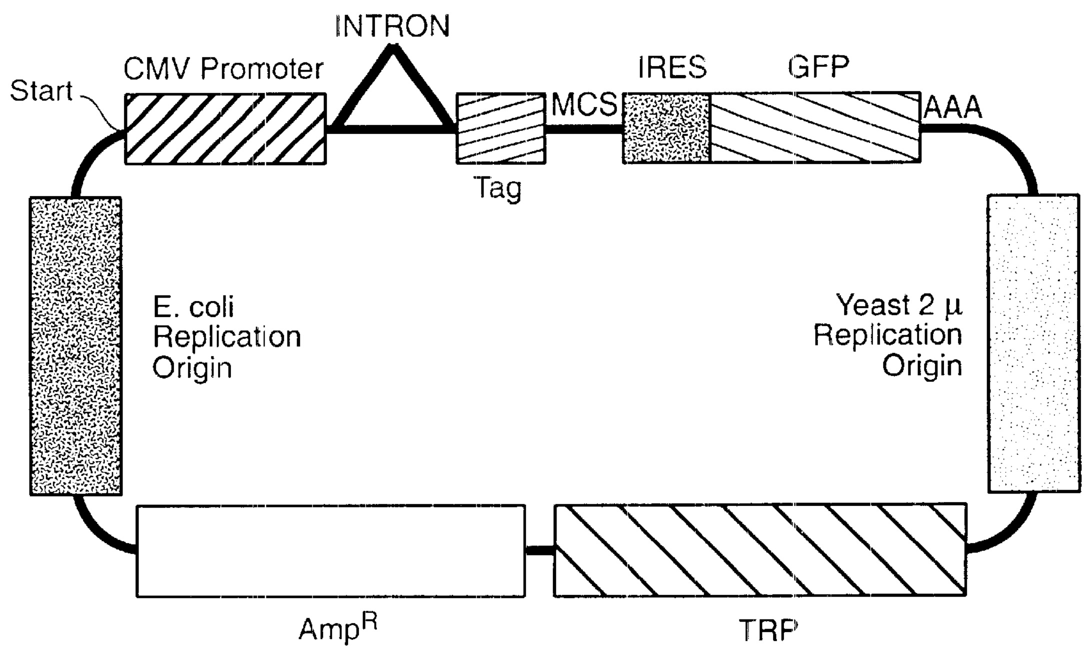
FIG._4

CAATGATGAGCACTTTTAAAGTTCTGCTATGTGGCGCGGTATTATCCCGTGTTGACGCCGGG
CAAGAGCAACTCGGTCGCCGCATACACTATTCTCAGAATGACTTGGTTGAGTACTCACCAGT
CACAGAAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAGT
TTACTCATATATACTTTAGATTGATTTGCGGCCGCAAACTTCATTTTTAATTTAAAAGGATC
TAGGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCC
TATGGAAAAACGCCAGCAACGCGGCCTTTTGCTCGAACGAAGCATCTGTGCTTCATTTTGTA
GAACAAAAATGCAACGCGAGAGCGCTAATTTTTCAAACAAAGAATCTGAGCTGCATTTTTAC
AGAACAGAAATGCAACGCGAAAGCGCTATTTTACCAACGAAGAATCTGTGCTTCATTTTTGT
AAAACAAAAATGCAACGCGAGAGCGCTAATTTTTCAAACAAAGAATCTGAGCTGCATTTTTA
CAGAACAGAAATGCAACGCGAGAGCGCTATTTTACCAACAAAGAATCTATACTTCTTTTTTG
TTCTACAAAAATGCATCCCGAGAGCGCTATTTTTCTAACAAAGCATCTTAGATTACTTTTTT
TCTCCTTTGTGCGCTCTATAATGCAGTCTCTTGATAACTTTTTGCACTGTAGGTCCGTTAAG
GTTAGAAGAAGGCTACTTTGGTGTCTATTTTCTCTTCCATAAAAAAAGCCTGACTCCACTTC
CCGCGTTTACTGATTACTAGCGAAGCTGCGGGTGCATTTTTTCAAGATAAAGGCATCCCCGA
TTATATTCTATACCGATGTGGATTGCGCATACTTTGTGAACAGAAAGTGATAGCGTTGATGA
TTCTTCATTGGTCAGAAAATTATGAACGGTTTCTTCTATTTTGTCTCTATATACTACGTATA
GGAAATGTTTACATTTTCGTATTGTTTTCGATTCACTCTATGAATAGTTCTTACTACAATTT
TTTTGTCTAAAGAGTAATACTAGAGATAAACATAAAAAATGTAGAGGTCGAGTTTAGATGCA
AGTTCAAGGAGCGAAAGGTGGATGGGTAGGTTATATAGGGATATAGCACAGAGATATATAGC
AAAGAGATACTTTTGAGCAATGTTTGTGGAAGCGGTATTCGCAATATTTTAGTAGCTCGTTA
CAGTCCGGTGCGTTTTTGGTTTTTTGAAAGTGCGTCTTCAGAGCGCTTTTGGTTTTCAAAAG
CGCTCTGAAGTTCCTATACTTTCTAGAGAATAGGAACTTCGGAATAGGAACTTCAAAGCGTT
TCCGAAAACGAGCGCTTCCGAAAATGCAACGCGAGCTGCGCACATACAGCTCACTGTTCACG
TCGCACCTATATCTGCGTGTTGCCTGTATATATATATACATGAGAAGAACGGCATAGTGCGT
GTTTATGCTTAAATGCGTACTTATATGCGTCTATTTATGTAGGATGAAAGGTAGTCTAGTAC
CTCCTGTGATATTATCCCATTCCATGCGGGGTATCGTATGCTTCCTTCAGCACTACCCTTTA
GCTGTTCTATATGCTGCCACTCCTCAATTGGATTAGTCTCATCCTTCAATGCTATCATTTCC
TTTGATATTGGATCATATTAAGAAACCATTATTATCATGACATTAACCTATAAAAATAGGCG
TATCACGAGGCCCTTTCGTCTCGCGCGTTTCGGTGATGACGGTGAAAACCTCTGACACATGC

FIG._2A

AGCTCCCGGAGACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCATCAGAGCAGAT
TGTACTGAGAGTGCACCATAGATCAACGACATTACTATATATATAATATAGGAAGCATTTAA
TAGACAGCATCGTAATATATGTGTACTTTGCAGTTATGACGCCAGATGGCAGTAGTGGAAGA
TATTCTTTATTGAAAAATAGCTTGTCACCTTACGTACAATCTTGATCCGGAGCTTTTCTTTT
TTTGCCGATTAAGAATTAATTCGGTCGAAAAAAGAAAAGGAGAGGGCCAAGAGGGAGGGCAT
TGGTGACTATTGAGCACGTGAGTATACGTGATTAAGCACACAAAGGCAGCTTGGAGTATGTC
TGTTATTAATTTCACAGGTAGTTCTGGTCCATTGGTGAAAGTTTGCGGCTTGCAGAGCACAG
AGGCCGCAGAATGTGCTCTAGATTCCGATGCTGACTTGCTGGGTATTATATGTGTGCCCAAT
AGAAAGAGAACAATTGACCCGGTTATTGCAAGGAAAATTTCAAGTCTTGTAAAAGCATATAA
AAATAGTTCAGGCACTCCGAAATACTTGGTTGGCGTGTTTCGTAATCAACCTAAGGAGGATG
TTTTGGCTCTGGTCAATGATTACGGCATTGATATCGTCCAACTGCATGGAGATGAGTCGTGG
CAAGAATACCAAGAGTTCCTCGGTTTGCCAGTTATTAAAAGACTCGTATTTCCAAAAGACTG
CAACATACTACTCAGTGCAGCTTCACAGAAACCTCATTCGTTTATTCCCTTGTTTGATTCAG
AAGCAGGTGGGACAGGTGAACTTTTGGATTGGAACTCGATTTCTGACTGGGTTGGAAGGCAA
GAGAGCCCCGAAAGCTTACATTTTATGTTAGCTGGTGGACTGACGCCAGAAAATGTTGGTGA
TGCGCTTAGATTAAATGGCGTTATTGGTGTTGATGTAAGCGGAGGTGTGGAGACAAATGGTG
TAAAAGACTCTAACAAAATAGCAAATTTCGTCAAAAATGCTAAGAAATAGGTTATTACTGAG
TAGTATTTATTTAAGTATTGTTTGTGCACTTGCCGATCACTATGGCCATTTAATGTAAATAC
TTAAGAAAAAAAACCAAATTAATTTTGATACATGCTGCATGTGAAGACCCCCGCTGACGGGT
AGTCAATCACTCAGAGGAGACCCTCCCAAGGCAGCGAGACCACAAGTCGGAAATGAAAGACC
CCCGCTGACGGGTAGTCAATCACTCAGAGGAGACCCTCCCAAGGAACAGCGAGACCACAAGT
CGGATGCAACTGCAAGAGGGTTTATTGGATACACGGGTACCCGGGCGACTCAGTCAATCGGA
GGACTGGCGCCCCGAGTGAGGGGTTGTGGGCTCTTTTATTGAGCTCGGGGAGCAGAAGCGCG
CGAACAGAAGCGAGAAGCGAACTGATTGGTTAGTTCAAATAAGGCACAGGGTCATTTCAGGT
CCTTGGGGCACCCTGGAAACATCTGATGGTTCTCTAGAAACTGCTGAGGGCTGGACCGCATC
TGGGGACCATCTGTTCTTGGCCCTGAGCCGGGGCAGGAACTGCTTACCACAGATATCCTGTT
TGGCCCATATTCAGCTGTTCCATCTGTTCTTGGCCCTGAGCCGGGGCAGGAACTGCTTACCA
CAGATATCCTGTTTGGCCCATATTCAGCTGTTCCATCTGTTCCTGACCTTGATCTGAACTTC
TCTATTCTCAGTTATGTATTTTTCCATGCCTTGCAAAATGGCGTTACTTAAGCTAGCTTGCC
AAACCTACAGGTGGGGTCTTTCATTCCCCCCTTTTTCTGGAGACTAAATAAAATCTTTTATT
TTATCGTCGATCGACTAGATCTTCAATATTGGCCATTAGCCATATTATTCATTGGTTATATA
GCATAAATCAATATTGGCTATTGGCCATTGCATACGTTGTATCTATATCATAATATGTACAT
TTATATTGGCTCATGTCCAATATGACCGCCATGTTGGCATTGATTATTGACTAGTTATTAAT
AGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTAC
GGTAAACTGCCCACTTGGCAGTACATCAAGTGTATCATATGCCAAGTCCGCCCCCTATTGAC
GTCAATGACGGTAAATGGCCCGCCTGGCATTATGCCCAGTACATGACCTTACGGGACTTTCC
TACTTGGCAGTACATCTACGTATTAGTCATCGCTATTACCATGGTGATGCGGTTTTGGCAGT
ACACCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATAAG
CAGAGCTCGTTTAGTGAACCGTCAGATCACTAGAAGCTTTATTGCGGTAGTTTATCACAGTT
AAATTGCTAACGCAGTCAGTGCTTCTGACACAACAGTCTCGAACTTAAGCTGCAGTGACTCT
CTTAAGGTAGCCTTGCAGAAGTTGGTCGTGAGGCACTGGGCAGGTAAGTATCAAGGTTACAA
GACAGGTTTAAGGAGACCAATAGAAACTGGGCTTGTCGAGACAGAGAAGACTCTTGCGTTTC
TGATAGGCACCTATTGGTCTTACTGACATCCACTTTGCCTTTCTCTCCACAGGTGTCCACTC

*FIG._2B*

CCAGTTCAATTACAGCTCTTAAGGCTAGAGTACTTAATACGACTCACTATAGGCTAGCCTCG
AGCCGCCACCATGGAATTCACGTGCATGCAGGCCTTAATTAAGTCGACACGTTATTTTCCAC
CATATTGCCGTCTTTTGGCAATGTGAGGGCCCGGAAACCTGGCCCTGTCTTCTTGACGAGCA
TTCCTAGGGGTCTTTCCCCTCTCGCCAAAGGAATGCAAGGTCTGTTGAATGTCGTGAAGGAA
GCAGTTCCTCTGGAAGCTTCTTGAAGACAAACAACGTCTGTAGCGACCCTTTGCAGGCAGCG
GAACCCCCCACCTGGCGACAGGTGCCTCTGCGGCCAAAAGCCACGTGTATAAGATACACCTG
CAAAGGCGGCACAACCCCAGTGCCACGTTGTGAGTTGGATAGTTGTGGAAAGAGTCAAATGG
CTCTCCTCAAGCGTATTCAACAAGGGGCTGAAGGATGCCCAGAAGGTACCCCATTGTATGGG
ATCTGATCTGGGGCCTCGGTGCACATGCTTTACATGTGTTTAGTCGAGGTTAAAAAACGTCT
AGGCCCCCCGAACCACGGGGACGTGGTTTTCCTTTGAAAAACACGATGATAATATGGGGAT
CCACCGGTCGCCACCATGGTGAGCAAGGGCGAGGAGCTGTTCACCGGGGTGGTGCCCATCCT
GGTCGAGCTGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCCGACCA
CATGAAGCAGCACGACTTCTTCAAGTCCGCCATGCCCGAAGGCTACGTCCAGGAGCGCACCA
TCTTCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGGGCA
CAAGCTGGAGTACAACTACAACAGCCACAACGTCTATATCATGGCCGACAAGCAGAAGAACG
GCATCAAGGTGAACTTCAAGATCCGCCACAACATCGAGGACGGCAGCGTGCAGCTCGCCGAC
CACTACCAGCAGAACACCCCCATCGGCGACGGCCCCGTGCTGCTGCCCGACAACCACTACCT
GAGCACCCAGTCCGCCCTGAGCAAAGACCCCAACGAGAAGCGCGATCACATGGTCCTGCTGG
AGTTCGTGACCGCCGCCGGGATCACTCTCGGCATGGACGAGCTGTACAAGTAAAGCGGCCGC
TCGACGATAAATTCCCTTTAGTGAGGGTTAATGCTTCGAGCAGACATGATAAGATACATTGA
TGAGTTTGGACAAACCACAACTAGAATGCAGTGAAAAAAATGCTCTATTTGTGAAATTTGTG
ATGCTATTGCTGTATTTGTAACCATTATAAGCTGCAATAAACAAGTTAACAACAACAATTGC
ATTCATTTTATGTTTCAGGTTCAGGGGGAGATGTGGGAGGTTTTTTAAAGCAAGTAAAACCT
CTACAAATGTGGTAAAATCCGATAAGGATCCGGCAGTCTAGAGGATGGTCCACCCCCGGGGT
CGGCAGCCTTCACGTGGCGGCGTGTATCCAAGCTGCGATGCCGTCTACTTTGAGGGCGGTG
GGGGTGGTCAGCAGGACTGTGTAAGGTCCTTTCCAGCGAGGTTCTAGGTTCTTAGTCTGGTG
TCGGCGGACCCACACTGTGTCGCCGACTCGGTAAGGGTGAGGTACCACCGGTCGGTCCAGTT
GTTCTTGGTACGTGCCGCCAGAGGTCTCCAGACTTCGTGCTGGACTAAGTAGAGAGCCTGTA
AGTGAGCTTGGAGAGAGGGGCTGTTAGTAACTCTTGTCATGTCAGGGTCAGGGAAGTTTACA
AGGGGCGGGGGTGCCCCATATAAGATCTCATATGGCCATATGGGGGCGCCTAGAGAAGGAGT
GAGGGCTGGATAAAGGGAGGATCGAGGCGGGGTCGAACGAGGAGGTTCAAGGGGGAGAGACG
GGGCGGATGGAGGAAGAGGAGGCGGAGGCTTAGGGTGTACAAAGGGCTTGACCCAGGGAGGG
GGGTCAAAAGCCAAGGCTTCCCAGGTCACGATGTAGGGGACCTGGTCTGGGTGTCCATGCGG
GCCAGGTGAAAAGACCTTGATCTTAACCTGGGTGATGAGGTCTCGGTTAAAGGTGCCGTCTC
GCGGCCATCCGACGTTAAAGGTTGGCCATTCTGCAGAGCAGAAGGTAACCCAACGTCTCTTC
TTGACATCTACCGACTGGTTGTGAGCGATCCGCTCGACATCTTTCCAGTGACCTAAGGTCAA
ACTTAAGGGAGTGGTAACAGTCTGGCCCGGGCCCATATTTTCAGACAAATACAGAAACACAG
TCAGACAGAGACAACACAGAACGATGCTGCAGCAGACAAGACGCGCGGCGCGGCTTCGGTCC
CAAACCGAAAGCAAAAATTCAGACGGAGGCGGGAACTGTTTTAGGTTCTCGTCTCCTACCAG
AACCACATATCCCTCCTCTAAGGGGGGTGCACCAAAGAGTCCAAAACGATCGGGATTTTTGG
ACTCAGGTCGGGCCACAAAAACGGCCCCCGAAGTCCCTGGGACGTCTCCCAGGGTTGCGGCC
GGGTGTTCCGAACTCGTCAGTTCCACCACGGGTCCGCCAGATACAGAGCTAGTTAGCTAACT
AGTACCGACGCAGGCGCATAAAATCAGTCATAGACACTAGACAATCGGACAGACACAGATAA
GTTGCTGGCCAGCTTACCTCCCGGTGGTGGGTCGGTGGTCCCTGGGCAGGGGTCTCCCGATC
CCGGACGAGCCCCCAAATGAAAGACCCCCGCTGACGGGTAGTCAATCACTCAGAGGAGACCC

FIG._2C

TCCCAAGGAACAGCGAGACCACAAGTCGGATGCAACTGCAAGAGGGTTTATTGGATACACGG
GTACCCGGGCGACTCAGTCAATCGGAGGACTGGCGCCCCGAGTGAGGGGTTGTGGGCTCTTT
TATTGAGCTCGGGGAGCAGAAGCGCGCGAACAGAAGCGAGAAGCGAACTGATTGGTTAGTTC
AAATAAGGCACAGGGTCATTTCAGGTCCTTGGGGCACCCTGGAAACATCTGATGGTTCTCTA
GAAACTGCTGAGGGCTGGACCGCATCTGGGGACCATCTGTTCTTGGCCCTGAGCCGGGGCAG
GAACTGCTTACCACAGATATCCTGTTTGGCCCATATTCAGCTGTTCCATCTGTTCTTGGCCC
TGAGCCGGGGCAGGAACTGCTTACCACAGATATCCGCTTTGGCCCATATTCAGCTGTTCCAT
CTGTTCCTGACCTTGATCTGAACTTTTCTATTCTCAGTTATGTATTTTTCCATGCCTTGCAA
AATGGCGTTACTTAAGCTAGCTTGCCAAACCTACAGGTGGGGTCTTTCACATGTATATGTCA
AAAATAAAAATCAACTAATTGACTAGTAATTAATATGACTGGCATAATGGGAAATTGATCCT
GACAGATGCAAACTGGCTTCTCAGCAGCGCATTTATGTTGTCAACTGAGGAAGGAAACGTTA
ATGACAGAAACTCTAAGTAATTTCCACGTTTATCTATTTTTATTTATACTAGCTTTGGTAAC
AGGAATATTGCAGCATTCATGCACATTGAAACCCTTATGAAATAAAAACATCTGTGCATTTA
AAATGGAATTAACATTTTAAATGTTAAAAAAAGCTGGCTTAGCTTCCCCCCGCCCCCTAGGG
CATAGAACAAGTCAAATGCTTTATATATTTGAGTTTGGGATGTATTAGGAAACTCCTAAGAG
CAAAGCTGTTCTTGAAGACGAAAGGGCCTCGTGATACGCCTATTTTTATAGGTTAATGTCAT
GAGACAATAACCCTGATAAATGCTTCAATAATATTGAAAAAGGAAGAGTATGAGTATTCAAC
ATTTCCGTGTCGCCCTTATTCCCTTTTTTGCGGCATTTTGCCTTCCTGTTTTTGCTCACCCA
GAAACGCTGGTGAAAGTAAAAGATGCTGAAGATCAGTTGGGTGCACGAGTGGGTTACATCGA
ACTGGATCTCAACAGCGGTAAGATCCTTGAGAGTTTTCGCCCCGAAGAACGTTTTC

FIG._2D

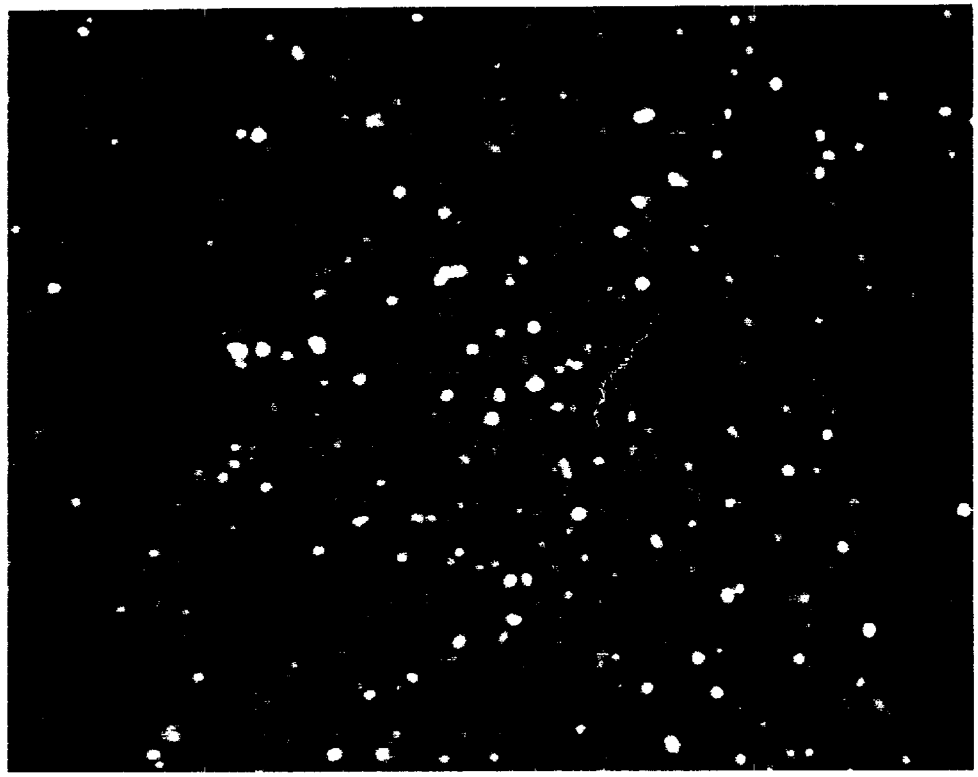
FIG._6
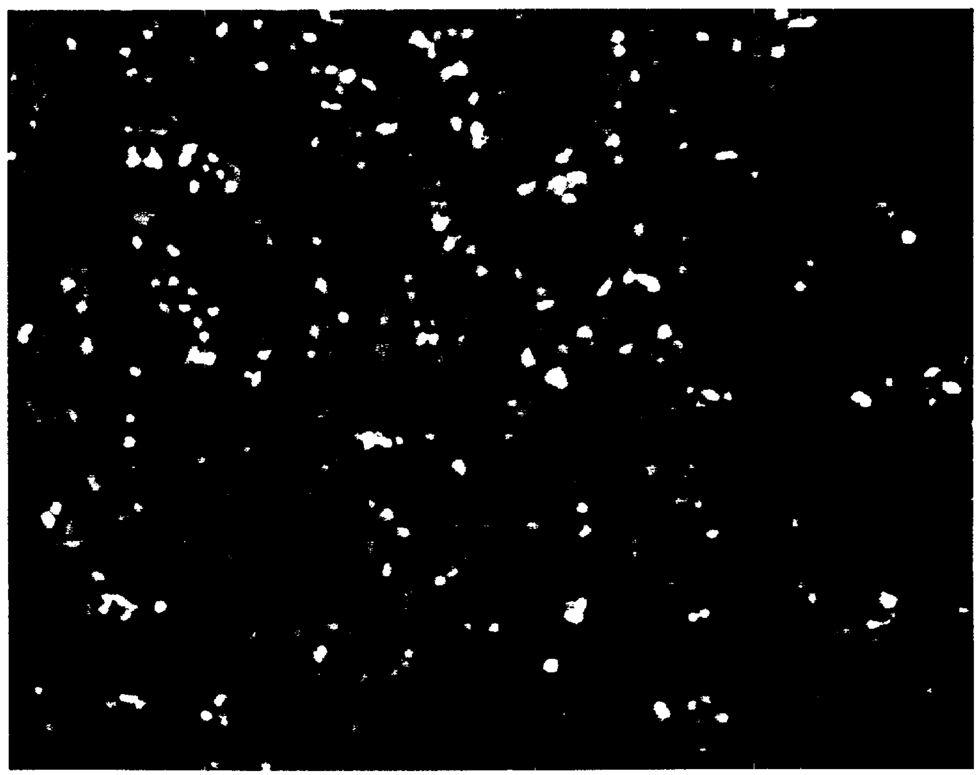
FIG._3

TCAATATTGGCCATTAGCCATATTATTCATTGGTTATATAGCATAAATCAATATTGGCTATT
GGCCATTGCATACGTTGTATCTATATCATAATATGTACATTTATATTGGCTCATGTCCAATA
TGACCGCCATGTTGGCATTGATTATTGACTAGTTATTAATAGTAATCAATTACGGGGTCATT
AGTTCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAACGCCA
ATAGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCCCG
CCTGGCATTATGCCCAGTACATGACCTTACGGGACTTTCCTACTTGGCAGTACATCTACGTA
TTAGTCATCGCTATTACCATGGTGATGCGGTTTTGGCAGTACACCAATGGGCGTGGATAGCG
GTTTGACTCACGGGGATTTCCAAGTCTCCACCCCATTGACGTCAATGGGAGTTTGTTTTGGC
ACCAAAATCAACGGGACTTTCCAAAATGTCGTAACAACTGCGATCGCCCGCCCCGTTGACGC
AAATGGGCGGTAGGCGTGTACGGTGGGAGGTCTATATAAGCAGAGCTCGTTTAGTGAACCGT
CAGATCACTAGAAGCTTTATTGCGGTAGTTTATCACAGTTAAATTGCTAACGCAGTCAGTGC
TTCTGACACAACAGTCTCGAACTTAAGCTGCAGTGACTCTCTTAAGGTAGCCTTGCAGAAGT
TGGTCGTGAGGCACTGGGCAGGTAAGTATCAAGGTTACAAGACAGGTTTAAGGAGACCAATA
GAAACTGGGCTTGTCGAGACAGAGAAGACTCTTGCGTTTCTGATAGGCACCTATTGGTCTTA
CTGACATCCACTTTGCCTTTCTCTCCACAGGTGTCCACTCCCAGTTCAATTACAGCTCTTAA
GGCTAGAGTACTTAATACGACTCACTATAGGCTAGCCGCCACCATGGCTTACCCATACGATG
TTCCAGATTACGCTGGGCAACCAGACATGTCCTTGAATGTCATTAAGATGAAATCCAGTGAC
TTCCTGGAGAGTGCAGAACTGGACAGCGGAGGCTTTGGGAAGGTGTCTCTGTGTTTCCACAG
AACCCAGGGACTCATGATCATGAAAACAGTGTACAAGGGGCCCAACTGCATTGAGCACAACG
AGGCCCTCTTGGAGGAGGCGAAGATGATGAACAGACTGAGACACAGCCGGGTGGTGAAGCTC
CTGGGCGTCATCATAGAGGAAGGGAAGTACTCCCTGGTGATGGAGTACATGGAGAAGGGCAA
CCTGATGCACGTGCTGAAAGCCGAGATGAGTACTCCGCTTTCTGTAAAAGGAAGGATAATTT
GGGAAATCATTGAAGGAATGTGCTACTTACATGAAAAGGCGTGATACACAAGGACCTGAAGC
CTGAAAATATCCTTGTTGATAATGACTTCCACATTAAGATCGCAGACCTCGGCCTTGCCTCC
TTTAAGATGTGGAGCAAACTGAATAATGAAGAGCACAATGAGCTGAGGGAAGTGGACGGCAC
CGCTAAGAAGAATGGCGGCACCCTCTACTACATGGCGCCCGAGCACCTGAATGACGTCAACG
CAAAGCCCACAGAGAAGTCGGATGTGTACAGCTTTGCTGTAGTACTCTGGGCGATATTTGCA
AATAAGGAGCCATATGAAAATGCTATCTGTGAGCAGCAGTTGATAATGTGCATAAAATCTGG
GAACAGGCCAGATGTGGATGACATCACTGAGTACTGCCCAAGAGAAATTATCAGTCTCATGA
AGCTCTGCTGGGAAGCGAATCCGGAAGCTCGGCCGACATTTCCTGGCATTGAAGAAAAATTT
AGGCCTTTTTATTTAAGTCAATTAGAAGAAAGTGTAGAAGAGGACGTGAAGAGTTTAAAGAA
AGAGTATTCAAACGAAAATGCAGTTGTGAAGAGAATGCAGTCTCTTCAACTTGATTGTGTGG
CAGTACCTTCAAGCCGGTCAAATTCAGCCACAGAACAGCCTGGTTCACTGCACAGTTCCCAG
GGACTTGGGATGGGTCCTGTGGAGGAGTCCTGGTTTGCTCCTTCCCTGGAGCACCCACAAGA
AGAGAATGAGCCCAGCCTGCAGAGTAAACTCCAAGACGAAGCCAACTACCATCTTTATGGCA
GCCGCATGGACAGGCAGACGAAACAGCAGCCCAGACAGAATGTGGCTTACAACAGAGAGGAG
GAAAGGAGACGCAGGGTCTCCCATGACCCTTTTGCACAGCAAAGACCTTACGAGAATTTTCA
GAATACAGAGGGAAAAGGCACTGTTTATTCCAGTGCAGCCAGTCATGGTAATGCAGTGCACC
AGCCCTCAGGGCTCACCAGCCAACCTCAAGTACTGTATCAGAACAATGGATTATATAGCTCA
CATGGCTTTGGAACAAGACCACTGGATCCAGGAACAGCAGGTCCCAGAGTTTGGTACAGGCC
AATTCCAAGTCATATGCCTAGTCTGCATAATATCCCAGTGCCTGAGACCAACTATCTAGGAA
ATACACCCACCATGCCATTCAGCTCCTTGCCACCAACAGATGAATCTATAAAATATACCATA
TACAATAGTACTGGCATTCAGATTGGAGCCTACAATTATATGGAGATTGGTGGGACGAGTTC
ATCACTACTAGACAGCACAAATACGAACTTCAAAGAAGAGCCAGCTGCTAAGTACCAAGCTA
TCTTTGATAATACCACTAGTCTGACGGATAAACACCTGGACCCAATCAGGGAAAATCTGGGA
AAGCACTGGAAAAACTGTGCCCGTAAACTGGGCTTCACACAGTCTCAGATTGATGAAATTGA

FIG._5A

CCATGACTATGAGCGAGATGGACTGAAAGAAAAGGTTTACCAGATGCTCCAAAAGTGGGTGA
TGAGGGAAGGCATAAAGGGAGCCACGGTGGGGAAGCTGGCCCAGGCGCTCCACCAGTGTTCC
AGGATCGACCTTCTGAGCAGCTTGATTTACGTCAGCCAGAACTAACACGCGTGGTACCTCTA
GAGTCGACACGTTATTTTCCACCATATTGCCGTCTTTTGGCAATGTGAGGGCCCGGAAACCT
GGCCCTGTCTTCTTGACGAGCATTCCTAGGGGTCTTTCCCCTCTCGCCAAAGGAATGCAAGG
TCTGTTGAATGTCGTGAAGGAAGCAGTTCCTCTGGAAGCTTCTTGAAGACAAACAACGTCTG
TAGCGACCCTTTGCAGGCAGCGGAACCCCCCACCTGGCGACAGGTGCCTCTGCGGCCAAAAG
CCACGTGTATAAGATACACCTGCAAAGGCGGCACAACCCCAGTGCCACGTTGTGAGTTGGAT
AGTTGTGGAAAGAGTCAAATGGCTCTCCTCAAGCGTATTCAACAAGGGGCTGAAGGATGCCC
AGAAGGTACCCCATTGTATGGGATCTGATCTGGGGCCTCGGTGCACATGCTTTACATGTGTT
TAGTCGAGGTTAAAAAACGTCTAGGCCCCCCGAACCACGGGGACGTGGTTTTCCTTTGAAAA
ACACGATGATAATATGGGGATCCACCGGTCGCCACCATGGTGAGCAAGGGCGAGGAGCTGT
TCACCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTGCAC
CACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAA
GGCTACGTCCAGGAGCGCACCATCTTCTTCAAGGACGACGGCAACTACAAGACCCGCGCCGA
GGTGAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATATC
ATGGCCGACAAGCAGAAGAACGGCATCAAGGTGAACTTCAAGATCCGCCACAACATCGAGGA
CGGCAGCGTGCAGCTCGCCGACCACTACCAGCAGAACACCCCCATCGGCGACGGCCCCGTGC
TGCTGCCCGACAACCACTACCTGAGCACCCAGTCCGCCCTGAGCAAAGACCCCAACGAGAAG
CGCGATCACATGGTCCTGCTGGAGTTCGTGACCGCCGCCGGGATCACTCTCGGCATGGACGA
GCTGTACAAGTAAAGCgGCCGCTTCCCTTTAGTGAGGGTTAATGCTTCGAGCAGACATGATA
AGATACATTGATGAGTTTGGACAAACCACAACTAGAATGCAGTGAAAAAAATGCTTTATTTG
TGAAATTTGTGATGCTATTGCTTTATTTGTAACCATTATAAGCTGCAATAAACAAGTTAACA
ACAACAATTGCATTCATTTTATGTTTCAGGTTCAGGGGGAGATGTGGGAGGTTTTTTAAAGC
AAGTAAAACCTCTACAAATGTGGTAAAATCCGATAAGGATCGATCCGGGCTGGCGTAATAGC
GAAGAGGCCCGCACCGATCGCCCTTCCCAACAGTTGCGCAGCCTGAATGGCGAATGGACGCG
CCCTGTAGCGGCGCATTAAGCGCGGCGGGTGTGGTGGTTACGCGCAGCGTGACCGCTACACT
TGCCAGCGCCCTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGAGCTTTACGG
CACCTCGACCGCAAAAAACTTGATTTGGGTGATGctcGAACGAAGCATCTGTGCTTCATTTT
GTAGAACAAAAATGCAACGCGAGAGCGCTAATTTTTCAAACAAAGAATCTGAGCTGCATTTT
TACAGAACAGAAATGCAACGCGAAAGCGCTATTTTACCAACGAAGAATCTGTGCTTCATTTT
TGTAAAACAAAAATGCAACGCGAGAGCGCTAATTTTTCAAACAAAGAATCTGAGCTGCATTT
TTACAGAACAGAAATGCAACGCGAGAGCGCTATTTTACCAACAAAGAATCTATACTTCTTTT
TTGTTCTACAAAAATGCATCCCGAGAGCGCTATTTTTCTAACAAAGCATCTTAGATTACTTT
TTTTCTCCTTTGTGCGCTCTATAATGCAGTCTCTTGATAACTTTTTGCACTGTAGGTCCGTT
AAGGTTAGAAGAAGGCTACTTTGGTGTCTATTTTCTCTTCCATAAAAAAAGCCTGACTCCAC
TTCCCGCGTTTACTGATTACTAGCGAAGCTGCGGGTGCATTTTTTCAAGATAAAGGCATCCC
CGATTATATTCTATACCGATGTGGATTGCGCATACTTTGTGAACAGAAAGTGATAGCGTTGA
TGATTCTTCATTGGTCAGAAAATTATGAACGGTTTCTTCTATTTTGTCTCTATATACTACGT
ATAGGAAATGTTTACATTTTCGTATTGTTTTCGATTCACTCTATGAATAGTTCTTACTACAA
TTTTTTTGTCTAAAGAGTAATACTAGAGATAAACATAAAAAATGTAGAGGTCGAGTTTAGAT
GCAAGTTCAAGGAGCGAAAGGTGGATGGGTAGGTTATATAGGGATATAGCACAGAGATATAT
AGCAAAGAGATACTTTTGAGCAATGTTTGTGGAAGCGGTATTCGCAATATTTTAGTAGCTCG
TTACAGTCCGGTGCGTTTTTGGTTTTTTGAAAGTGCGTCTTCAGAGCGCTTTTGGTTTTCAA

FIG._5B

AAGCGCTCTGAAGTTCCTATACTTTCTAGAGAATAGGAACTTCGGAATAGGAACTTCAAAGC
GTTTCCGAAAACGAGCGCTTCCGAAAATGCAACGCGAGCTGCGCACATACAGCTCACTGTTC
ACGTCGCACCTATATCTGCGTGTTGCCTGTATATATATATACATGAGAAGAACGGCATAGTG
CGTGTTTATGCTTAAATGCGTACTTATATGCGTCTATTTATGTAGGATGAAAGGTAGTCTAG
TACCTCCTGTGATATTATCCCATTCCATGCGGGGTATCGTATGCTTCCTTCAGCACTACCCT
TTAGCTGTTCTATATGCTGCCACTCCTCAATTGGATTAGTCTCATCCTTCAATGCTATCATT
TCCTTTGATATTGGATCATATTAAGAAACCATTATTATCATGACATTAACCTATAAAAATAG
GCGTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTATGCGGCATCAGAGCA
GATTGTACTGAGAGTGCACCATAGATCAACGACATTACTATATATATAATATAGGAAGCATT
TAATAGACAGCATCGTAATATATGTGTACTTTGCAGTTATGACGCCAGATGGCAGTAGTGGA
AGATATTCTTTATTGAAAAATAGCTTGTCACCTTACGTACAATCTTGATCCGGAGCTTTTCT
TTTTTTGCCGATTAAGAATTAATTCGGTCGAAAAAAGAAAAGGAGAGGGCCAAGAGGGAGGG
CATTGGTGACTATTGAGCACGTGAGTATACGTGATTAAGCACACAAAGGCAGCTTGGAGTAT
GTCTGTTATTAATTTCACAGGTAGTTCTGGTCCATTGGTGAAAGTTTGCGGCTTGCAGAGCA
CAGAGGCCGCAGAATGTGCTCTAGATTCCGATGCTGACTTGCTGGGTATTATATGTGTGCCC
AATAGAAAGAGAACAATTGACCCGGTTATTGCAAGGAAAATTTCAAGTCTTGTAAAAGCATA
TAAAAATAGTTCAGGCACTCCGAAATACTTGGTTGGCGTGTTTCGTAATCAACCTAAGGAGG
ATGTTTTGGCTCTGGTCAATGATTACGGCATTGATATCGTCCAACTGCATGGAGATGAGTCG
TGGCAAGAATACCAAGAGTTCCTCGGTTTGCCAGTTATTAAAAGACTCGTATTTCCAAAAGA
CTGCAACATACTACTCAGTGCAGCTTCACAGAAACCTCATTCGTTTATTCCCTTGTTTGATT
CAGAAGCAGGTGGGACAGGTGAACTTTTGGATTGGAACTCGATTTCTGACTGGGTTGGAAGG
CAAGAGAGCCCCGAAAGCTTACATTTTATGTTAGCTGGTGGACTGACGCCAGAAAATGTTGG
TGATGCGCTTAGATTAAATGGCGTTATTGGTGTTGATGTAAGCGGAGGTGTGGAGACAAATG
GTGTAAAAGACTCTAACAAAATAGCAAATTTCGTCAAAAATGCTAAGAAATAGGTTATTACT
GAGTAGTATTTATTTAAGTATTGTTTGTGCACTTGCCGATCGCGTATGGTGCACTCTCAGTA
CAATCTGCTCTGATGCCGCATAGTTAAGCCAGCCCCGACACCCGCCAACACCCGCTGACGCG
CCCTGACGGGCTTGTCTGCTCCCGGCATCCGCTTACAGACAAGCTGTGACCGTCTCCGGGAG
CTGCATGTGTCAGAGGTTTTCACCGTCATCACCGAAACGCGCGAGACGAAAGGGCCTCGTGA
TACGCCTATTTTTATAGGTTAATGTCATGATAATAATGGTTTCTTAGACGTCAGGTGGCACT
TTTCGGGGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCCGTATTGACGCC
GGGCAAGAGCAACTCGGTCGCCGCATACACTATTCTCAGAATGACTTGGTTGAGTACTCACC
AGTCACAGAAAAGCATCTTACGGATGGCATGACAGTAAGAGAATTATGCAGTGCTGCCATAA
CCATGAGTGATAACACTGCGGCCAACTTACTTCTGACAACGATCGGAGGACCGAAGGAGCTA
ACCGCTTTTTTGCACAACATGGGGGATCATGTAACTCGCCTTGATCGTTGGGAACCGGAGCT
GAATGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGACTGG
ATGGAGGCGGATAAAGTTGCAGGACCACTTCTGCGCTCGGCCCTTCCGGCTGGCTGGTTTAT
TGCTGATAAATCTGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACCA
AGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA

FIG._5C

GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGCCTTTTGCTCACA
TGGCTCGACAGATCT

FIG._5D

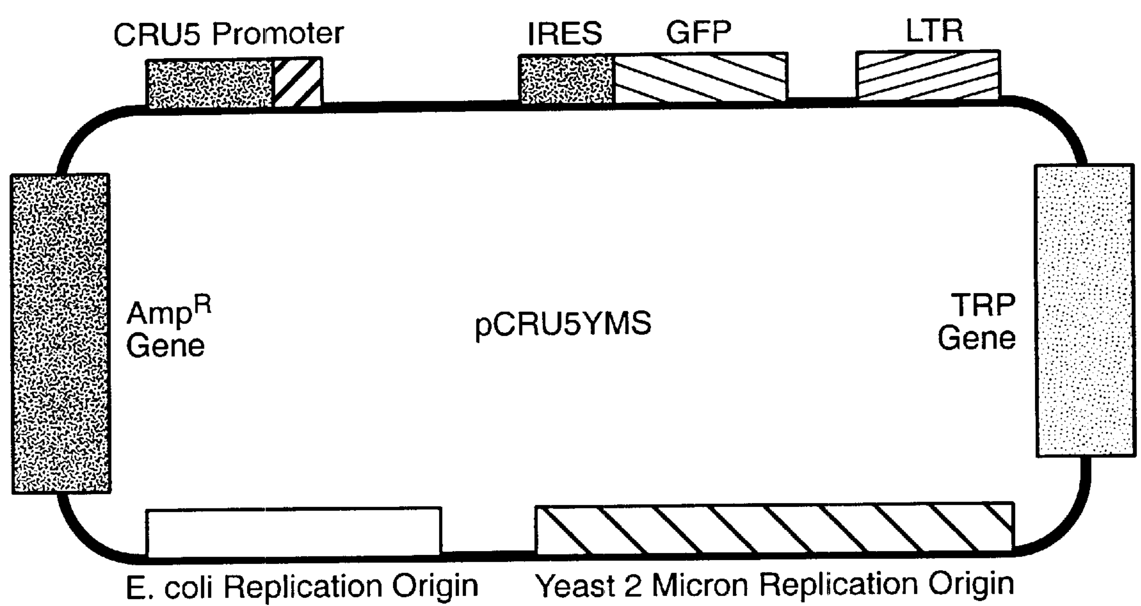
FIG._7

ATCACGAGGCCCTTTCGTCTTCAAGAACAGCTTTGCTCTTAGGAGTTTCCTAATACATCCCA
AACTCAAATATATAAAGCATTTGACTTGTTCTATGCCCTAGTTATTAATAGTAATCAATTAC
GGGGTCATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTCCCATA
GTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGGTA
AATGGCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATGGGCG
TGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACG
CAAATGGGCGGTAGGCATGTACGGTGGGAGGTCTATATAAGCAGAGCTCAATAAAAGAGCCC
ACAACCCCTCACTCGGGGCGCCAGTCCTCCGATTGACTGAGTCGCCCGGGTACCCGTGTATC
CAATAAACCCTCTTGCAGTTGCATCCGACTTGTGGTCTCGCTGTTCCTTGGGAGGGTCTCCT
CTGAGTGATTGACTACCCGTCAGCGGGGGTCTTTCATTTGGGGGCTCGTCCGGGATCGGGAG
ACCCCTGCCCAGGGACCACCGACCCACCACCGGGAGGTAAGCTGGCCAGCAACTTATCTGTG
TCTGTCCGATTGTCTAGTGTCTATGACTGATTTTATGCGCCTGCGTCGGTACTAGTTAGCTA
ACTAGCTCTGTATCTGGCGGACCCGTGGTGGAACTGACGAGTTCGGAACACCCGGCCGCAAC
CCTGGGAGACGTCCCAGGGACTTCGGGGGCCGTTTTTGTGGCCCGACCTGAGTCCAAAAATC
CCGATCGTTTTGGACTCTTTGGTGCACCCCCCTTAGAGGAGGGATATGTGGTTCTGGTAGGA
GACGAGAACCTAAAACAGTTCCCGCCTCCGTCTGAATTTTTGCTTTCGGTTTGGGACCGAAG
CCGCGCCGCGCGTCTTGTCTGCTGCAGCATCGTTCTGTGTTGTCTCTGTCTGACTGTGTTTC
TGTATTTGTCTGAAAATATCGGCCCGGGCCAGACTGTTACCACTCCCTTAAGTTTGACCTTA
GGTCACTGGAAAGATGTCGAGCGGATCGCTCACAACCAGTCGGTAGATGTCAAGAAGAGACG
TTGGGTTACCTTCTGCTCTGCAGAATGGCCAACCTTTAACGTCGGATGGCCGCGAGACGGCA
CCTTTAACCGAGACCTCATCACCCAGGTTAAGATCAAGGTCTTTTCACCTGGCCCGCATGGA
CACCCAGACCAGGTCCCCTACATCGTGACCTGGGAAGCCTTGGCTTTTGACCCCCCTCCCTG
GGTCAAGCCCTTTGTACACCCTAAGCCTCCGCCTCCTCTTCCTCCATCCGCCCCGTCTCTCC
CCCTTGAACCTCCTCGTTCGACCCCGCCTCGATCCTCCCTTTATCCAGCCCTCACTCCTTCT
CTAGGCGCCCCCATATGGCCATATGAGATCTTATATGGGGCACCCCCGCCCCTTGTAAACTT
CCCTGACCCTGACATGACAAGAGTTACTAACAGCCCCTCTCTCCAAGCTCACTTACAGGCTC
TCTACTTAGTCCAGCACGAAGTCTGGAGACCTCTGGCGGCAGCCTACCAAGAACAACTGGAC
CGACCGGTGGTACCTCACCCTTACCGAGTCGGCGACACAGTGTGGGTCCGCCGACACCAGAC
TAAGAACCTAGAACCTCGCTGGAAAGGACCTTACACAGTCCTGCTGACCACCCCCACCGCCC
TCAAAGTAGACGGCATCGCAGCTTGGATACACGCCGCCCACGTGAAGGCTGCCGACCCCGGG
GGTGGACCATCCTCTAGACTGCCGGATCTCGAGGGATCCACCACCATGGACCCCCATTAAAT
TGGAATTCCTGCAGCCCGGGGGATCCACTAGTTCTAGAGCGAATTAATTCCGGTTATTTTCC
ACCATATTGCCGTCTTTTGGCAATGTGAGGGCCCGGAAACCTGGCCCTGTCTTCTTGACGAG
CATTCCTAGGGGTCTTTCCCCTCTCGCCAAAGGAATGCAAGGTCTGTTGAATGTCGTGAAGG
AAGCAGTTCCTCTGGAAGCTTCTTGAAGACAAACAACGTCTGTAGCGACCCTTTGCAGGCAG
CGGAACCCCCCACCTGGCGACAGGTGCCTCTGCGGCCAAAAGCCACGTGTATAAGATACACC
TGCAAAGGCGGCACAACCCCAGTGCCACGTTGTGAGTTGGATAGTTGTGGAAAGAGTCAAAT
GGCTCTCCTCAAGCGTATTCAACAAGGGGCTGAAGGATGCCCAGAAGGTACCCCATTGTATG
GGATCTGATCTGGGGCCTCGGTGCACATGCTTTACATGTGTTTAGTCGAGGTTAAAAAACGT
CTAGGCCCCCCGAACCACGGGGACGTGGTTTTCCTTTGAAAAACACGATGATAATATGGGGG
ATCCACCGGTCGCCACCATGGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGAGGG
CGATGCCACCTACGGCAAGCTGACCCTGAAGTTCATCTGCACCACCGGCAAGCTGCCCGTGC
CCTGGCCCACCCTCGTGACCACCCTGACCTACGGCGTGCAGTGCTTCAGCCGCTACCCCGAC

FIG._8A

CACATGAAGCAGCACGACTTCTTCAAGTCCGCCATGCCCGAAGGCTACGTCCAGGAGCGCAC
CATCTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTGGGG
CACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACAACCACTAC
CTGAGCACCCAGTCCGCCCTGAGCAAAGACCCCAACGAGAAGCGCGATCACATGGTCCTGCT
GGAGTTCGTGACCGCCGCCGGGATCACTCTCGGCATGGACGAGCTGTACAAGTAAAGCGGCC
GCTCGACGATAAAATAAAAGATTTTATTTAGTCTCCAGAAAAAGGGGGGAATGAAAGACCCC
ACCTGTAGGTTTGGCAAGCTAGCTTAAGTAACGCCATTTTGCAAGGCATGGAAAAATACATA
ACTGAGAATAGAGAAGTTCAGATCAAGGTCAGGAACAGATGGAACAGCTGAATATGGGCCAA
ACAGGATATCTGTGGTAAGCAGTTCCTGCCCCGGCTCAGGGCCAAGAACAGATGGAACAGCT
GAATATGGGCCAAACAGGATATCTGTGGTAAGCAGTTCCTGCCCCGGCTCAGGGCCAAGAAC
AGATGGTCCCCAGATGCGGTCCAGCCCTCAGCAGTTTCTAGAGAACCATCAGATGTTTCCAG
GGTGCCCCAAGGACCTGAAATGACCCTGTGCCTTATTTGAACTAACCAATCAGTTCGCTTCT
CGCTTCTGTTCGCGCGCTTCTGCTCCCCGAGCTCAATAAAAGAGCCCACAACCCCTCACTCG
GGGCGCCAGTCCTCCGATTGACTGAGTCGCCCGGGTACCCGTGTATCCAATAAACCCTCTTG
CAGTTGCATCCGACTTGTGGTCTCGCTGTTCCTTGGGAGGGTCTCCTCTGAGTGATTGACTA
CCCGTCAGCGGGGGTCTTTCATTTCCGACTTGTGGTCTCGCTGCCTTGGGAGGGTCTCCTCT
GAGTGATTGACTACCCGTCAGCGGGGGTCTTCACATGCAGCATGTATCAAAATTAATTTGGT
TTTTTTTCTTAAGTATTTACATTAAATGGCCATAGTGATCGGCAAGTGCACAAACAATACTT
AAATAAATACTACTCAGTAATAACCTATTTCTTAGCATTTTTGACGAAATTTGCTATTTTGT
TAGAGTCTTTTACACCATTTGTCTCCACACCTCCGCTTACATCAACACCAATAACGCCATTT
AATCTAAGCGCATCACCAACATTTTCTGGCGTCAGTCCACCAGCTAACATAAAATGTAAGCT
TTCGGGGCTCTCTTGCCTTCCAACCCAGTCAGAAATCGAGTTCCAATCCAAAAGTTCACCTG
TCCCACCTGCTTCTGAATCAAACAAGGGAATAAACGAATGAGGTTTCTGTGAAGCTGCACTG
AGTAGTATGTTGCAGTCTTTTGGAAATACGAGTCTTTTAATAACTGGCAAACCGAGGAACTC
TTGGTATTCTTGCCACGACTCATCTCCATGCAGTTGGACGATATCAATGCCGTAATCATTGA
CCAGAGCCAAAACATCCTCCTTAGGTTGATTACGAAACACGCCAACCAAGTATTTCGGAGTG
CCTGAACTATTTTTATATGCTTTTACAAGACTTGAAATTTTCCTTGCAATAACCGGGTCAAT
TGTTCTCTTTCTATTGGGCACACATATAATACCCAGCAAGTCAGCATCGGAATCTAGAGCAC
ATTCTGCGGCCTCTGTGCTCTGCAAGCCGCAAACTTTCACCAATGGACCAGAACTACCTGTG
AAATTAATAACAGACATACTCCAAGCTGCCTTTGTGTGCTTAATCACGTATACTCACGTGCT
CAATAGTCACCAATGCCCTCCCTCTTGGCCCTCTCCTTTTCTTTTTTCGACCGAATTAATTC
TTAATCGGCAAAAAAAGAAAAGCTCCGGATCAAGATTGTACGTAAGGTGACAAGCTATTTTT
CAATAAAGAATATCTTCCACTACTGCCATCTGGCGTCATAACTGCAAAGTACACATATATTA
CGATGCTGTCTATTAAATGCTTCCTATATTATATATATATAGTAATGTCGTTGATCTATGGTGC
ACTCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGAGACGAAAG
GGCCTCGTGATACGCCTATTTTTATAGGTTAATGTCATGATAATAATGGTTTCTTAATATGA
TCCAATATCAAAGGAAATGATAGCATTGAAGGATGAGACTAATCCAATTGAGGAGTGGCAGC
ATATAGAACAGCTAAAGGGTAGTGCTGAAGGAAGCATACGATACCCCGCATGGAATGGGATA
ATATCACAGGAGGTACTAGACTACCTTTCATCCTACATAAATAGACGCATATAAGTACGCAT
TTAAGCATAAACACGCACTATGCCGTTCTTCTCATGTATATATATATACAGGCAACACGCAG
ATATAGGTGCGACGTGAACAGTGAGCTGTATGTGCGCAGCTCGCGTTGCATTTTCGGAAGCG
CTCGTTTTCGGAAACGCTTTGAAGTTCCTATTCCGAAGTTCCTATTCTCTAGAAAGTATAGG
AACTTCAGAGCGCTTTTGAAAACCAAAAGCGCTCTGAAGACGCACTTTCAAAAAACCAAAAA

FIG._8B

CGCACCGGACTGTAACGAGCTACTAAAATATTGCGAATACCGCTTCCACAAACATTGCTCAA
AAGTATCTCTTTGCTATATATCTCTGTGCTATATCCCTATATAACCTACCCATCCACCTTTC
GCTCCTTGAACTTGCATCTAAACTCGACCTCTACATTTTTTATGTTTATCTCTAGTATTACT
CTTTAGACAAAAAAATTGTAGTAAGAACTATTCATAGAGTGAATCGAAAACAATACGAAAAT
GTAAACATTTCCTATACGTAGTATATAGAGACAAAATAGAAGAAACCGTTCATAATTTTCTG
ACCAATGAAGAATCATCAACGCTATCACTTTCTGTTCACAAAGTATGCGCAATCCACATCGG
TATAGAATATAATCGGGGATGCCTTTATCTTGAAAAAATGCACCCGCAGCTTCGCTAGTAAT
CAGTAAACGCGGGAAGTGGAGTCAGGCTTTTTTTATGGAAGAGAAAATAGACACCAAAGTAG
CCTTCTTCTAACCTTAACGGACCTACAGTGCAAAAAGTTATCAAGAGACTGCATTATAGAGC
GCACAAAGGAGAAAAAAAGTAATCTAAGATGCTTTGTTAGAAAAATAGCGCTCTCGGGATGC
ATTTTTGTAGAACAAAAAAGAAGTATAGATTCTTTGTTGGTAAAATAGCGCTCTCGCGTTGC
ATTTCTGTTCTGTAAAAATGCAGCTCAGATTCTTTGTTTGAAAAATTAGCGCTCTCGCGTTG
CATTTTTGTTTTACAAAAATGAAGCACAGATTCTTCGTTGGTAAAATAGCGCTTTCGCGTTG
CATTTCTGTTCTGTAAAAATGCAGCTCAGATTCTTTGTTTGAAAAATTAGCGCTCTCGCGTT
GCATTTTTGTTCTACAAAATGAAGCACAGATGCTTCGTTCGAGCAAAAGGCCAGCAAAAGGC
CAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCT
CTGCTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAA
GGGATTTTGGTCATGAGATTATCAAAAAGGATCTTCACCTAGATCCTTTTAAATTAAAAATG
AAGTTTGCGCAAATCAATCTAAAGTATATATGAGTAAACTTGGTCTGACAGTTACCAATGCT
TAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATCAA
GGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAACACGGGATAATACC
GCGCCACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAACTGAT
CTTCAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCAATA
TTATTGAAGCATTTATCAGGGTTATTGTCTCATGACATTAACCTATAAAAATAGGCGT

FIG._8C

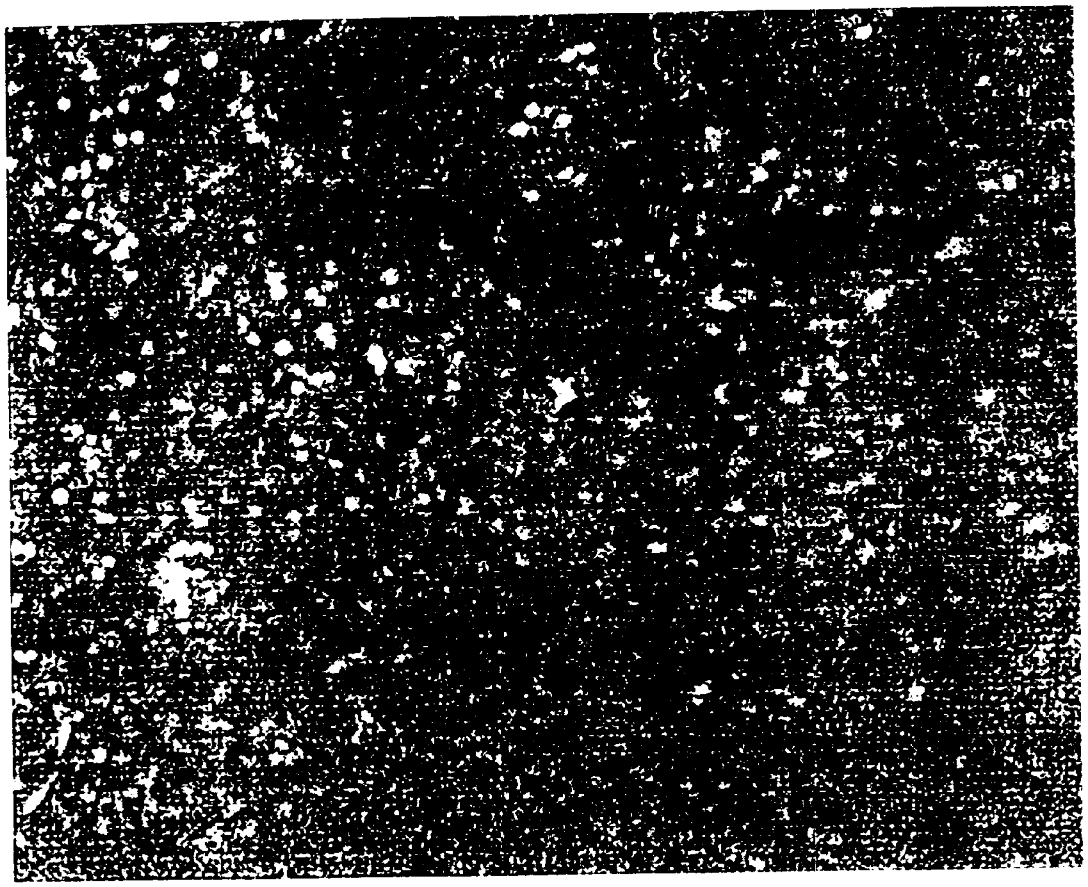
FIG._9

SHUTTLE VECTORS

This is a continuation of application Ser. No. 09/208,827 filed on Dec. 9, 1998 and now U.S. Pat. No. 6,391,582 and for which the Issue Fee was paid on Dec. 28, 2001, and Ser. No. 09/133,944, filed on Aug. 14, 1998 now U.S. Pat. No. 6,280,937 issued on Aug. 28, 2001.

FIELD OF THE INVENTION

The invention relates to novel shuttle vectors, and more particularly, shuttle vectors capable of replication in at least yeast and capable of expression in at least a mammalian cell.

BACKGROUND OF THE INVENTION

The introduction of cloned nucleotide sequences into mammalian cells has greatly facilitated the study of the control and function of various eukaryotic genes. Mammalian cells provide an environment conducive to appropriate protein folding, post translational processing, feedback control, protein-protein interactions, and other eukaryotic protein modifications such as glycosylation and oligomerization. Thus, a number of expression vectors have been developed which allow the expression of a polypeptide in a mammalian cell.

The typical mammalian expression vector will contain (1) regulatory elements, usually in the form of a viral promoter or enhancer sequences; (2) a multicloning site, usually having specific enzyme restriction sites to facilitate the insertion of a DNA fragment with the vector; and (3) sequences responsible for intron splicing and polyadenylation of mRNA transcripts. Generally, sequences facilitating the replication of the vector in both bacterial and mammalian hosts and a selection marker gene which allows selection of transformants in bacteria are also included. The bacterial elements, or in some cases phage elements, are included to provide the option of further analyzation of the nucleic acid inserts amplified and isolated from the bacteria or phage.

In the past, the insertion of a heterologous nucleic acid (insert) into the multicloning site of a mammalian expression vector has generally been accomplished by one of two methods. In the first method, the insert is cut out of a bacterial expression vector and ligated into the mammalian expression vector. In the second method, often called "TA cloning", special ends are generated on the insert by PCR such that the modified insert can be put into the mammalian expression vector. Each of these methods requires a number of steps including enzymatic reactions which can be labor intensive and unreliable. Moreover, cloning efficiency drops significantly as the size of the insert increases.

Another method used for inserting a heterologous nucleic acid (insert) into an expression vector takes advantage of yeast's high efficiency at homologous recombination in vivo. In this method, a nucleic acid fragment flanked by 5' and 3' homologous regions is co-introduced into a yeast with a vector which has regions identical to the 5' and 3' regions flanking the fragment. The yeast efficiently homologously recombines such that the fragment inserts into the region of the vector flanked by the before-mentioned 5' and 3' regions. H. a., et al., *Plasmid,* 38:91–96 (1997), incorporated herein. Unfortunately, yeast are the only organisms able to efficiently recombine so as to insert heterologous nucleic acids into a vector. Therefore, to date, there is not an efficient method or means to transfer inserts into a specific region of a vector used for expression in mammalian cells.

Accordingly, it is an object of the invention to provide compositions and methods useful in facilitating the insertion of a heterologous nucleic acid into a vector which can express the heterologous nucleic acid in at least a mammalian cell.

Moreover, it is the object of this invention to provide a shuttle vector and methods of use which allow replication of the shuttle vector at least in yeast and which allow expression in at least a mammalian cell.

SUMMARY OF THE INVENTION

The invention provides shuttle vectors, and methods of using shuttle vectors, capable of expression in at least a mammalian cell. Furthermore, the shuttle vectors are capable of replication in at least yeast, and optionally, bacterial cells.

In one aspect of the invention, the invention provides a shuttle vector comprising an origin of replication functional in yeast and preferably, a reporter gene functional in yeast. The shuttle vector further comprises a promoter functional in a mammalian cell, capable of directing transcription of a polypeptide coding sequence operably linked to said promoter.

In another aspect of the invention, the shuttle vector comprises an insertion site operably linked to said promoter. The insertion site preferably allows for homologous recombination with a heterologous nucleic acid. In one embodiment, the insertion site has 5' and 3' regions identical to 5' and 3' regions flanking a nucleic acid to be inserted into the vector.

Optionally, the shuttle vector comprises any one or more of the following: an internal ribosome entry sequence (IRES), a polyadenylation sequence and a splice sequence.

In another aspect of the invention, the shuttle vector further comprises an origin of replication functional in a bacterial cell and preferably, a selectable gene functional in a bacterial cell. The shuttle vector may also comprise an origin of replication functional in a mammalian cell, and optionally, a selectable gene functional in a mammalian cell.

The present invention also provides methods for using the shuttle vectors provided herein. In one embodiment, heterologous nucleic acids flanked by regions identical to flanking regions of the insertion site within a shuttle vector are co-introduced to yeast with the shuttle vector and allowed to homologously recombine such that the heterologous nucleic acids are inserted into the shuttle vector by the yeast organism. In preferred embodiments, the heterologous nucleic acids are introduced to the yeast in a linear nucleic acid. The shuttle vector is then recovered and transferred to a mammalian cell for expression.

BRIEF DESCRIPTION OF THE DRAWINGS

FIG. 1 is a schematic of a shuttle vector in accordance with the present invention referred to herein as pPYC-R. The following abbreviations are used herein: IRES for internal ribosomal binding site, GFP for a green florescence protein, $Amp^R$ for an Ampicillin resistance gene, TRP for a tryptophan gene, and MCS for multi-cloning site or sequence.

FIGS. 2A through 2D show the nucleotide sequence (SEQ ID NO:1) of pPYC-R. In SEQ ID NO:1, a CMV promoter is at nucleotides 4853–5614, an IRES is at nucleotides 6001–6505, a GFP gene is at nucleotides 6506–7258, an $Amp^R$ gene is at nucleotides 9888–655, an *E. coli* origin of replication site is at nucleotides 656–1456, a yeast $2\mu$ origin of replication is at nucleotides 1461–2808, and a TRP gene is at nucleotides 3344–4018. The intron contains 5' and 3' splice sites.

FIG. 3 is a photograph showing the results of a mammalian cell transfection assay using the shuttle vector pPYC-R.

FIG. 4 is a schematic of a shuttle vector in accordance with the present invention referred to herein as pPYC.

FIGS. 5A through 5D show the nucleotide sequence (SEQ ID NO:2) of pPYC. In SEQ ID NO:2, a CMV promoter is at nucleotides 1–750, an IRES site is at nucleotides 1158–1662, a GFP gene is at nucleotides 1683–2402, a yeast 2$\mu$ origin of replication is at nucleotides 2985–4332, a tryptophan gene is at nucleotides 4868–5542, an Ampicillin resistance gene is at nucleotides 5982–6842, and an *E. coli* origin or replication is at nucleotides 7142–7669. The tag is hemagglutinin (HA).

FIG. 6 is a photograph showing pPYC transfection wherein pPYC includes a gene causing apoptosis in accordance with the present invention. The photograph shows extensive cell death due to the expression of HA tagged Rip.

FIG. 7 is a schematic of a shuttle vector in accordance with the present invention referred to herein as pCRU5YMS.

FIGS. 8A through 8C show the nucleotide sequence (SEQ ID NO:5) of pCRU5YMS. At nucleotides 1–664 is the CMV promoter; at nucleotides 2197–2725 is the IRES. At nucleotides 2746–3465 is the GFP gene; at nucleotides 3522–4252 is the LTR; and at nucleotides 4253–5500 is the Yeast selection marker TRP gene. At nucleotides 5512–6860 is the Yeast 2 micron replication origin; at nucleotides 6861–7650 is the *E. coli* replication origin and at nucleotides 7678–8538 is the Ampicillin resistance gene.

FIG. 9 is a photograph showing the results of a mammalian cell transfection assay using the shuttle vector pCRU5YMS.

DETAILED DESCRIPTION OF THE INVENTION

The invention provides shuttle vectors, and methods of use, wherein the shuttle vectors are capable of expression in at least a mammalian cell and capable of replication in at least yeast. In the past, vectors have been constructed so as to be functional in certain aspects either in mammalian cells or yeast, but not both. As described herein, different hosts provide different advantages to an expression vector and in particular, to the expression product. By providing a vector which is functional as described herein in multiple hosts, the invention allows the advantages provided by varying hosts to be obtained by the use of a single tool.

For example, a vector having the ability to replicate in yeast is useful for a variety of reasons. An advantage of the yeast system is its efficiency at homologous recombination. Orr-Weaver, et al., *PNAS USA,* 80:4417–4421 (1983), incorporated herein by reference. By taking advantage of yeast's ability to insert heterologous nucleic acids into a vector, this eliminates the steps of manipulating the ends of the vector and the heterologous nucleic acid and ligating the two together. Another advantage of this system is that yeast can be transformed with large nucleic acids, i.e., up to at least 10 kilobases, which can then be inserted into the vector.

Moreover, yeast is a well-studied organism which facilitates its use. In particular, yeast has been widely used to detect protein-protein interactions in the "two-hybrid system". The two-hybrid system is a method used to identify and clone genes for proteins that interact with a protein of interest. Briefly, the system indicates protein-protein interaction by the reconstitution of GAL4 function, which is detectable and only occurs when the proteins interact. This system and general methodologies concerning the transformation of yeast with expressible vectors are described in Cheng-Ting et al., PNAS USA, 88:9578–9582 (1991), Fields and Song, Nature, 340:245–246 (1989), and Chevray and Nathans, PNAS USA, 89:5789–5793 (1992), each incorporated herein in their entirety.

Regarding mammalian cells, these cells are preferred for the expression of eukaryotic proteins particularly when determining or studying the function of the protein. Mammalian cells are able to reproduce the protein's proper glycosylation and oligomerization, folding, post translational processing, feedback control, protein-protein interaction, etc., and thus are advantageous for expression of eukaryotic and particularly mammalian proteins.

Regarding bacterial cells or phage, these systems are also very well studied and are therefore easily manipulated. In particular, bacteria and phage are useful for the rapid amplification of nucleic acids.

Thus, while vectors which function in one of yeast, mammalian cells, bacteria or phage are useful, vectors which can successfully shuttle between these systems are particularly desirable. This invention provides such vectors. In a preferred embodiment, the shuttle vector functions in both yeast and mammalian cells. Such a shuttle vector can allow for the exploitation of the yeast two-hybrid system as well as yeast's ability to homologously recombine, as well as provide a convenient means for subsequent expression in mammalian cells to, for example, verify protein-protein interactions, study the protein's function, etc.

In one embodiment, the invention provides a shuttle vector comprising an origin of replication functional in yeast and a promoter functional in a mammalian cell. Preferably, the shuttle vector also comprises a selectable gene functional in yeast.

The origin of replication functional in yeast is any nucleic acid sequence which allows replication of the shuttle vector independently from the chromosome. Generally, the origin of replication is functional in at least one or more of the following: *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. Suitable origin of replication sites include, for example, ars 1, centromere ori, and 2$\mu$ ori. Yeast origin of replication sites can be used to increase the copy number and to retrieve the vector from yeast.

The "promoter functional in a mammalian cell" or "mammalian promoter" is capable of directing transcription of a polypeptide coding sequence operably linked to said promoter. The choice of the promoter will depend in part on the mammalian cell into which the vector is put. Generally, this promoter is functional in at least one or more of the following: Chinese hamster ovary (CHO), BHK, 293, Hela, NH3T3 and COS cells. More specific examples include monkey kidney CV1 line; human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Transcription from vectors in mammalian host cells is controlled, for example, by promoters obtained from the genomes of viruses such as adenoviruses, retroviruses, lentiviruses, herpes viruses, including but not limited to, polyoma virus, fowlpox virus (UK 2,211,504 published Jul. 5, 1989), adenovirus 2, bovine papilloma virus, avian sarcoma virus, cytomegalovirus (CMV), hepatitis-B virus, Simian Virus 40 (SV40), Epstein Barr virus (EBV), feline immunedeficiency virus (FIV), and Srα, or are respiratory synsitial viral promoters (RSV) or long terminal repeats (LTRs) of a retrovirus, i.e., a Moloney Murine Leukemia Virus (MoMuLv) (Cepko et al. (1984) *Cell* 37:1053–1062). Moreover, the promoters can be selected from heterologous mammalian promoters, e.g., the actin promoter or an immunoglobulin promoter, and from heat-shock promoters, and functional derivatives thereof, provided such promoters are compatible with the host cell systems. The promoter functional in a mammalian cell can be inducible or constitutive.

In an embodiment provided herein, the shuttle vector is double stranded and on a first strand, comprises a first promoter operably linked to either a coding sequence or a site for the insertion of a coding sequence of interest (i.e., a heterologous nucleic acid) followed by a polyadenylation site. On a second strand, the shuttle vector comprises two LTRs flanking said region comprising said first promoter and coding sequence or cloning site, wherein the LTRs operate in a direction opposite to said first promoter.

"Operably linked" as used herein means that the transcriptional and translational regulatory nucleic acid is positioned relative to any coding sequences in such a manner that transcription is initiated. Generally, this will mean that the promoter and transcriptional initiation or start sequences are positioned 5' to the coding region. The transcriptional and translational regulatory nucleic acid will generally be appropriate to the host cell used, as will be appreciated by those in the art.

By "vector" or "episome" herein is meant a nucleic acid replicon used for the transformation of host cells. The vectors may be either self-replicating extrachromosomal vectors or vectors which integrate into a mammalian host genome, such as a retroviral based vector. In a preferred embodiment, the shuttle vector remains as an extrachromosomal vector in bacteria and yeast, and is integrated into the genome of the mammalian cell.

A preferred embodiment utilizes retroviral desired vectors. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins -gag, pol, and env-that are required for packaging, processing, reverse transcription, and integration of recombinant genomes. Those RNA molecules that have in cis the ψ packaging signal are packaged into maturing virions. In addition, transfection efficiencies of retroviruses can be extremely high, thus obviating the need for selection genes in some cases.

Retroviral transfection systems are further described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); WO 94/19478; PCT U.S.97/01019, and references cited therein, all of which are incorporated by reference.

Any number of suitable retroviral vectors may be used to construct the shuttle vectors of the invention. Preferred retroviral vectors include a vector based on the murine stem cell virus (MSCV) (see Hawley et al., Gene Therapy 1:136 (1994)) and a modified MFG virus (Rivere et al., Genetics 92:6733 (1995)), and pBABE (see PCT U.S.97/01019, incorporated by reference), and functional derivatives thereof.

In addition, it is possible to configure a retroviral vector to allow expression of genes after integration in target cells. For example, Tet-inducible retroviruses can be used to express genes (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population.

The shuttle vector can also be based on a non-retroviral vector. Any number of known vectors are suitable, including, but not limited to, pREP9, pCDNA, pCEP4 (Invitrogen), pCI and pCI-NEO (Promega). Basically, any vector can be reconstructed to contain the components as described herein. For example, construction of suitable vectors containing the components described herein can be achieved by employing standard ligation techniques which are known to the skilled artisan, using cloned or synthetic sequences.

In a preferred embodiment, the shuttle vector includes a selectable gene functional in yeast (also referred to herein as a yeast reporter gene). By "selectable gene" or "reporter gene" herein is meant a gene that by its presence in a host cell, i.e. upon expression, can allow the host to be distinguished from a cell that does not contain the selectable gene. Selectable genes can be classified into several different types, including survival and detection genes. It may be the nucleic acid or the protein expression product that causes the effect. Additional components, such as substrates, ligands, etc., may be additionally added to allow selection or sorting on the basis of the selectable gene.

In a preferred embodiment, the selectable gene is a survival gene that serves to provide a nucleic acid (or encode a protein) without which the cell cannot survive, such as a drug resistant gene, a growth regulatory gene, or a nutritional requirement. The selectable gene functional in yeast is preferably a survival gene. Wherein a selectable gene functional in bacteria is included in the shuttle vector, a survival gene is also preferred.

Preferred survival genes functional in yeast are survival genes which include ADE2, HIS3, LEU2, TRP1, URA3, and ALG7, which confer resistance to tunicamycin; the neomycin phosphotransferase gene, which confers resistance to G418; the CUP1 gene, which allows yeast to grow in the presence of copper ions; and an adenine producing gene, or the like, which may be used alone or in combinations of two or more thereof. In a preferred embodiment, the trp1 gene is utilized. Stinchcomb et al., *Nature,* 282:39 (1979); Kingsman et al., *Gene,* 7:141 (1979); Tschemper et al., *Gene,* 10:157 (1980). The trp1 gene provides a selection marker for a mutant strain of yeast lacking the ability to grow in tryptophan, for example, ATCC No. 44076 or PEP4-1 [Jones, *Genetics,* 85:12 (1977)]. The preferred selectable gene functional in bacteria is a drug resistant, such as an ampicillin resistant gene.

In a preferred embodiment, the selectable gene is a detection gene. Wherein a selectable gene functional in mammalian cells is included in the vector, a detection gene is preferred. Detection genes encode a protein that can be used as a direct or indirect label, i.e., for sorting the cells, i.e. for cell enrichment by FACS. In this embodiment, the protein product of the selectable gene itself can serve to distinguish cells that are expressing the selectable gene. In this embodiment, suitable selectable genes include those encoding green fluorescent protein (GFP), blue fluorescent protein (BFP), yellow fluorescent protein (YFP), red fluorescent protein (RFP), luciferase, β-galactosidase, all commercially available, i.e., Clontech, Inc.

Alternatively, the selectable gene encodes a protein that will bind a label that can be used as the basis of selection; i.e. the selectable gene serves as an indirect label or detection gene. In this embodiment, the selectable gene should encode a cell-surface protein. For example, the selectable gene may be any cell-surface protein not normally expressed on the surface of the cell, such that secondary binding agents could serve to distinguish cells that contain the selectable gene from those that do not. Alternatively, albeit non-preferably, selectables comprising normally expressed cell-surface proteins could be used, and differences between cells containing the selectable construct and those without could be determined. Thus, secondary binding agents bind to the selectable protein. These secondary binding agents are preferably labeled, for example with fluors, and can be antibodies, haptens, etc. For example, fluorescently labeled antibodies to the selectable gene can be used as the label. Similarly, membrane-tethered streptavidin could serve as a selectable gene, and fluorescent biotin could be used as the label, i.e. the secondary binding agent. Alternatively, the secondary binding agents need not be labeled as long as the secondary binding agent can be used to distinguish the cells containing the construct; for example, the secondary binding agents may be used in a column, and the cells passed through, such that the expression of the selectable gene results in the cell being bound to the column, and a lack of the selectable gene (i.e. inhibition), results in the cells not being retained on the column. Other suitable selectable proteins/secondary labels include, but are not limited to, antigens and antibodies, enzymes and substrates (or inhibitors), etc.

In one aspect of the invention, the shuttle vector includes an insertion site, which is used to insert a heterologous nucleic acid sequence of choice, for ultimate expression in mammalian cells. The insertion site can be either be a cloning site, preferably a multicloning site (MCS), or a site suitable for homologous recombination, (referred to herein as a homologous recombination site). The vector can include multiple insertion sites, including both cloning sites and at least one homologous recombination site.

In a preferred embodiment, the insertion site is a cloning site. A cloning site as used herein is a known sequence, preferably the only one on the vector, (i.e., it is a unique sequence on the vector) upon which a restriction enzyme operates to linearize or cut the vector. A multicloning site, also sometimes referred to as a multiple cloning site, polylinker, or polycloning site, is a cluster of cloning sites such that many restriction enzymes operate thereon. A wide variety of these sites are known in the art.

In a preferred embodiment, the insertion site is a site that allows the introduction of the heterologous nucleic acid into the shuttle vector by homologous recombination. Homologous recombination is, briefly, the process of strand exchange that can occur spontaneously with the alignment of homologous sequences (i.e. sets of complementary strands). As is known in the art, yeast are efficient at homologous recombination. Orr-Weaver, et al, supra; H. a., et al., supra; Ma, et al., *Gene,* 58:201–216 (1987); Petermann, *Nucleic Acids Res.,* 26(9):2252–2253 (1998); each incorporated herein by reference. Thus, in general, the homologous recombination site contains two distinct, but generally contiguous, regions. The first region, referred to herein as the 5' region, is generally identical to the 5' region flanking the heterologous nucleic acid to be inserted into the vector. The second region, referred to herein as the 3' region, is generally identical to the 3' region flanking the heterologous nucleic acid to be inserted into the vector. Preferably, the 5' and 3' regions are each at least 12 or 15 nucleic acids long. More preferably, the 5' and 3' regions are each at least about 20 or 30 nucleic acids long, and more preferably at least about 50 nucleic acids long, and most preferably about 60 nucleic acids long. These regions are preferably less than about 100 nucleic acids long. Preferably, the homologous recombination site sequence is unique to the vector in that the vector does not comprise another sequence corresponding to the sequence of the homologous recombination site.

The insertion site is used to insert a heterologous nucleic acid. A "heterologous nucleic acid" as used herein refers to any nucleic acid inserted into the shuttle vector at a site operably linked to the promoter. Various embodiments of heterologous nucleic acids are further defined below. In a preferred embodiment, the heterologous nucleic acid is flanked by 5' and 3' regions identical to the 5' and 3' regions of a homologous recombination site on the shuttle vector provided herein. Thus, when the heterologous nucleic acid is inserted into the vector, the 5' and 3' regions flanking the heterologous nucleic acid replace the 5' and 3' regions of the homologous recombination site during homologous recombination.

In a further aspect, the shuttle vector further comprises an origin of replication flunctional in a bacterial cell. The bacterial cell is generally any bacterial cell which can be used to amplify the shuttle vector. Examples include Gram-negative or Gram-positive organisms, for example, Enterobacteriaceae such as *E. coli, Bacillus subtilis, Streptococcus cremoris, Streptococcus lividans*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Origin of replication sites are known in the art and are further described in Sambrook, et al., *Molecular Cloning,* 2nd Ed., Vol. 3, Chapter 1, particularly sections 12–20 (1989), Promega, 1998 catalog number E1841 (pCI-neo).

In one embodiment, the shuttle vector also comprises an origin of replication functional in mammalian cells. As is known in the art, the only extrachromosomal vectors which replicate in mammalian cells are virally derived. A number of viral origin of replications require the binding of a specific viral replication protein to effect replication. Suitable origin of replication/viral replication protein pairs include, but are not limited to, the Epstein Barr origin of replication and the Epstein Barr nuclear antigen (see Sugden et al., Mole. Cell. Biol. 5(2):410–413 (1985)); the SV40 origin of replication and the SV40 T antigen (see Margolskee et al., Mole. Cell. Biol. 8(7):2837 (1988)). The coding sequence for the viral replication protein can be on the shuttle vector provided herein, or on a separate vector.

In an additional aspect of this invention, the shuttle vector comprises additional sequences, including but not limited to at least one or all of the following: an internal ribosome entry sequence (IRES), an RNA splice site (also called a splice signal or sequence herein) and a polyadenylation site (also called a polyadenylation signal or sequence herein).

IRES elements function as initiators of the efficient translation of reading frames. In particular, IRES allows for the translation of two different genes on a single transcript. IRES thus greatly facilitates the selection of cells expressing peptides at uniformly high levels. IRES elements are known in the art and are further characterized in Kim, et al., Molecular and Cellular Biology 12(8):3636–3643 (August 1992) and McBratney, et al., Current Opinion in Cell Biology 5:961–965 (1993).

All of those sequences of viral, cellular, or synthetic origin which mediate an internal binding of the ribosomes can be used as an IRES. Examples include those IRES elements from poliovirus Type I, the 5'UTR of encephalomyocarditis virus (EMV), of "Thelier's murine encephalomyelitis virus (TMEV) of "foot and mouth disease virus" (FMDV) of "bovine enterovirus (BEV), of "coxsackie B virus" (CBV), or of "human rhinovirus" (HRV), or the "human immunoglobulin heavy chain binding protein" (BIP) 5'UTR, the *Drosophila antennapediae* 5'UTR or the *Drosophila ultrabithorax* 5'UTR, or genetic hybrids or fragments from the above-listed sequences.

The shuttle vectors provided herein may include a splice donor and acceptor site (splicing signals or splice sites) within the transcription unit. Splicing signals are known to increase mRNA stability and protein expression levels. Splicing signals are known in the art and are further described in Sambrook, et al., *Molecular Cloning,* 2nd Ed., Vol. 3, Chapter 16, particularly section 7 (1989).

A polyadenylation site or signal refers to sequences necessary for the termination of transcription and for stabilizing the mRNA of eukaryotes. Such sequences are commonly available and are further described in Sambrook, et al., *Molecular Cloning,* 2nd Ed., Vol. 3, Chapter 16, particularly sections 6–7 (1989).

Optionally, the shuttle vector may further comprise transcription enhancers. Enhancers are cis-acting elements of DNA, usually about from 10 to 300 bp, that act on a promoter to increase its transcription. Many enhancer sequences are now known from mammalian genes including for example, globin, elastase, albumin, α-fetoprotein, and insulin. Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to a coding sequence, but is preferably located at a site 5' from the promoter.

Optionally, the vector can be constructed so as to allow of the heterologous nucleic acid expression in yeast and/or bacterial cells. In this embodiment, the vector would further include a promoter functional in yeast and/or bacterial cells. Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Promoters for bacterial cells are known in the art and further described i.e., in Sambrook, et al., *Molecular Cloning,* 2nd Ed., Vol. 3, Chapter 17, particularly sections 11–17 (1989). Generally, promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence.

In an embodiment provided herein, the insertion site is linked to a selection system, i.e., a detection gene. In a preferred embodiment, from the 5' to 3' direction the construct comprises the mammalian promoter, the heterologous nucleic acid, the IRES site, and the selectable gene.

In a preferred embodiment, the vectors are used to screen heterologous nucleic acids. "Heterologous nucleic acids" as used herein refers to naturally occurring nucleic acids, random nucleic acids, or "biased" random nucleic acids, e.g. in nucleotide/residue frequency generally or per position. By "randomized" or grammatical equivalents herein is meant that each nucleic acid consists of essentially random nucleotides. For example, digests of procaryotic or eukaryotic genomes may be used, or cDNA fragments. They are heterologous in that they are inserted into the shuttle vector.

In a preferred embodiment, the heterologous nucleic acids are presented to the shuttle vector in the form of a cloning vector wherein the heterologous nucleic acid is flanked by 5' and 3' regions identical to 5' and 3' regions of an insertion site (i.e., a homologous recombination site) on the shuttle vector. That is, heterologous nucleic acids are recombined into cloning vectors containing homologous recombination flanking regions. The cloning vectors and the shuttle vectors are introduced into yeast, where recombination takes place. In a preferred embodiment, the cloning vectors are linear when introduced to the yeast.

In one aspect of the invention, the shuttle vectors provided herein are used to transform yeast. Heterologous nucleic acids are then, or simultaneously introduced to the yeast, and in a preferred embodiment, homologous recombination takes place such that the yeast inserts the heterologous nucleic acid into the shuttle vector at a specific insertion site, i.e., a homologous recombination site.

Transformations into yeast are typically carried out according to the method of Van Solingen et al., *J. Bact.,* 130:946 (1977) and Hsiao et al., *Proc. Natl. Acad. Sci.,* (*USA*), 76:3829 (1979). The shuttle vectors are then isolated from the yeast and used to transform mammalian cells for expression of the heterologous nucleic acid.

For transforming mammalian cells, the calcium phosphate precipitation method of Graham and van der Eb, *Virology,* 52:456–457 (1978) can be employed. General aspects of mammalian cell host system transformations have been described in U.S. Pat. No. 4,399,216. However, other methods for introducing DNA into cells, such as by nuclear microinjection, biolistics, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al.,

*Nature,* 336:348–352 (1988). Expression in mammalian cells is also described in Sambrook, et al., *Molecular Cloning,* 2nd Ed., Vol. 3, Chapter 16, particularly sections 68–72 (1989).

Isolation of the shuttle vectors is performed by standard techniques known in the art. Generally, the shuttle vectors can be isolated by breaking the cell open and separating the vector nucleic acid based on weight, i.e., centrifugation, or size, i.e. gel permeability. The vectors need only be isolated to the extent required to perform transformation.

In one aspect of this invention, the invention involves expression of heterologous nucleic acid inserts in a mammalian cell population. The expression of heterologous nucleic acids is identified by the production of a label or tag. Thus, when the shuttle vector expresses a heterologous nucleic acid, a selectable gene will also be expressed thereby verifying the presence of an expressed heterologous nucleic acid.

In another aspect of the present invention, expressed heterologous nucleic acids are selected on the basis of activity or phenotype. For example, the expressed insert or the cell type expressing that particular insert can be screened for its ability to interact with an antibody or ligand, capable of specific binding to the encoded product of that insert, which has been previously bound to a solid support such as a petri dish. Positive cDNA inserts (those expressed in cell types binding to the solid support) are recovered, transformed into a convenient host (*E.coli*) and characterized by known recombinant DNA techniques. This procedure is also referred to as panning, and is further described in Wysocki and Sata, 1979 PNAS 75:2844–2848 and Seen and Aruffo, 1987 PNAS 84:3365–3369.

Thus, in one embodiment, the present invention allows for creating shuttle vectors with inserts therein, without necessarily requiring the skilled artisan to insert the heterologous nucleic acid into the shuttle vector. Rather, the invention herein provides for the yeast organism to perform this step in a preferred embodiment. Moreover, the present invention also allows for expression in mammalian cells, which provides for a native environment for expressing mammalian genes. Additionally, the invention provides for a variety of options, such as replication in bacteria for amplification of shuttle vectors containing selected heterologous nucleic acids. Moreover, the shuttle vectors provided herein can perform the traditional aspects of expression vectors, whether or not "shuttling" is desired.

Furthermore, the present invention provides for screening for heterologous nucleic acids which encode candidate agents. "Candidate agents" as used herein are peptides which may have a desired effect on the phenotype or genotype of a cell. Heterologous nucleic acids expressing a candidate agent can be designed in a number of ways so as to facilitate their identification. Generally, this is achieved by the use of fusion partners, or combinations of fusion partners. Examples include presentation structures, targeting sequences, rescue sequences, and stability sequences, all of which can be used independently or in combination, with or without linker sequences.

By "fusion partner" or "functional group" herein is meant a sequence that is associated with the heterologous nucleic acid expressing a candidate agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In a preferred embodiment, the fusion partner is a presentation structure. By "presentation structure" or grammatical equivalents herein is meant a sequence, which, when fused to a heterologous nucleic acid expressing a candidate agent, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGCAALESEVSALESEVASLESEVAALGRGDMPLAAVKSKLSAVKSKLASVKSKLAACGPP (SEQ ID NO:6). The underlined regions represent a coiled-coil leucine zipper region defined previously (see Martin et al., EMBO J. 13(22):5303–5309 (1994), incorporated by reference). The bolded GRGDMP region represents the loop structure and when appropriately replaced with randomized peptides (i.e., candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQATSGFTFSHFYMEWVRGGEYIAASR HKHNKYTTEYSASVKGR YIVSRDTSQSILYLQKKKGPP (SEQ ID NO:7). The bold, underline regions are the regions which may be randomized. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Arg Lys Val) (SEQ ID NO:8), Kalderon (1984), et al., Cell, 39:499–509; the human retinoic acid receptor-β nuclear localization signal (ARRRRP) (SEQ ID NO:9); NFκB p50 (EEVQRKRQKL (SEQ ID NO:10); Ghosh et al., Cell 62:1019 (1990)); NFκB p65 (EEKRKRTYE (SEQ ID NO:11); Nolan et al., Cell 64:961 (1991)); and others (see for example Boulikas, J. Cell. Biochem. 55(1):32–58 (1994), hereby incorporated by reference) and double basic NLSs exemplified by that of the Xenopus (African clawed toad) protein, nucleoplasmin (Ala Val Lys Arg Pro Ala Ala Thr Lys Lys Ala Gly Gin Ala Lys Lys Lys Lys Leu Asp) (SEQ ID NO: 12), Dingwall, et al., Cell, 30:449–458, 1982 and Dingwall, et al., J. Cell Biol., 107:641–849; (1988). Numerous localization studies have demonstrated that NLSs incorporated in synthetic peptides or grafted onto selectable proteins not normally targeted to the cell nucleus cause these peptides and selectable proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized epression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:13); Nakauchi et al., PNAS USA 82:5126 (1985)) and 1–21 in the case of ICAM-2 (MSSFGYRTLTVALFTLICCPG (SEQ ID NO:14); Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDCRPRGSVKGTGLDFACDIYIWAPLAGICVA LLLSLIITLICYHSR (SEQ ID NO:15); Nakauchi, supra) and 224–256 from ICAM-2 (MVIIVTVVSVLLSLFVTSVLLCFIFGQHLRQQR (SEQ ID NO:16); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO: 17), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:18) (see Cross et al., Mol. Cell. Biol. 4(9):1834 (1984); Spencer et al., Science 262:1019–1024 (1993), both of which are hereby incorporated by reference). This motif has already been shown to be effective in the localization of selectable genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO:19), with the bold cysteines being palmitolyated; Stoffel et al., J. Biol. Chem 269:27791 (1994)); from rhodopsin (KQFRNCMLTSLCCGKNPLGD (SEQ ID NO:20); Barnstable et al., J. Mol. Neurosci. 5(3):207 (1994)); and the p21 H-ras 1 protein (LNPPDESGPGCMSCKCVLS (SEQ ID NO:21); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:22); Dice, Ann. N.Y. Acad. Sci. 674:58 (1992)); or lysosomal membrane sequences from Lamp-1 (MLIPIAGFFALAGLVLIVLIAYLIGRKRSHAGYQTI (SEQ ID NO :23), Uthayakumar et al., Cell. Mol. Biol. Res. 41:405 (1995)) or Lamp-2 (LVPIAVGAALAGVLILVLLAYFIGLKHHHAGYEQF (SEQ ID NO:24), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSSLFTRRVQPSLFSRNILRLQST (SEQ ID NO:25); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:26); Schatz, supra); mitochondrial intermembrane space sequences (yeast cytochrome c1; MFSMLSKRWAQRTLSKSFYSTATGAASKSGKLTQKLVTAGVAAAGITAST LLYADSLTAEAMTA (SEQ ID NO:27); Schatz, supra) or mitochondrial outer membrane sequences (yeast 70 kD outer membrane protein; MKSFITRNKTAILATVAATGTAIGAYYYYNQLQQQQQRGKK (SEQ ID NO:28); Schatz, supra).

The target sequences may also be endoplasmic reticulum sequences, including the sequences from calreticulin (KDEL (SEQ ID NO:29); Pelham, Royal Society London Transactions B; 1–10 (1992)) or adenovirus E3/19K protein (LYLSRRSFIDEKKMP (SEQ ID NO:30); Jackson et al., EMBO J. 9:3153 (1990)).

Furthermore, targeting sequences also include peroxisome sequences (for example, the peroxisome matrix sequence from Luciferase; SKL (SEQ ID NO:32); Keller et al., PNAS USA 4:3264 (1987)); farnesylation sequences (for example, P21 H-ras 1; LNPPDESGPGCMSCKCVLS (SEQ ID NO:31), with the bold cysteine farnesylated; Capon, supra); geranylgeranylation sequences (for example, protein rab-5A; LTEPTQPTRNQCCSN (SEQ ID NO:33), with the bold cysteines geranylgeranylated; Farnsworth, PNAS USA 91:11963 (1994)); or destruction sequences (cyclin B1; RTALGDIGN (SEQ ID NO:34); Klotzbucher Ct al., EMBO J. 1:3053 (1996)).

In a preferred embodiment, the targeting sequence is a secretory signal sequence capable of effecting the secretion of the candidate agent. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:35); Villinger et al., J. Immunol. 155:3946 (1995)), growth hormone (MATGSRTSLLLAFGLLCLPWLQEGSA<u>FPT</u> (SEQ ID NO:36); Roskam et al., Nucleic Acids Res. 7:30 (1979)); preproinsulin (MALWMRLLPLLALLALWGPDPAAA<u>FVN</u> (SEQ ID NO:37); Bell et al., Nature 284:26 (1980)); and influenza HA protein (MKAKLLVLLYAFVAG<u>DQI</u> (SEQ ID NO:38); Sekikawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLACAGNFVHG (SEQ ID NO:39).

In a preferred embodiment, the fusion partner is a rescue sequence. A rescue sequence is a sequence which may be used to purify or isolate either the candidate agent or the heterologous nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the heterologous nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the pro lines impart both flexibility and prevent structure initiating events in the di-proline to be propagated into the candidate peptide structure. Thus, preferred stability sequences are as follows: $MG(X)_nGGPP$, where X is any amino acid and n is an integer of at least four (SEQ ID NO:40).

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods.

The fusion partners may be placed anywhere (i.e. N-terminal, C-terminal, internal) in the structure as the biology and activity permits.

In a preferred embodiment, the fusion partner includes a linker or tethering sequence, as generally described in PCT U.S. 97/01019, that can allow the candidate agents to interact with potential targets unhindered. For example, when the candidate bioactive agent is a peptide, useful linkers include glycine-serine polymers (including, for example, $(GS)_n$ (SEQ ID NO:41), $(GSGGS)_n$ (SEQ ID NO:42) and $(GGGS)_n$ (SEQ ID NO:43), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

Thus, heterologous nucleic acids can be sequences which have not been manipulated in any way, or alternatively, they can be constructed to have fusion partners. In either case, they can be inserted into the shuttle vectors by conventional methods such as enzymatic manipulation and ligation, or preferably, are inserted into the shuttle vector by homologous recombination as described herein.

It is understood by the skilled artisan that while various options (of compounds, properties selected or order of steps) are provided herein, the options are also each provided individually, and can each be individually segregated from the other options provided herein. Moreover, steps which are obvious and known in the art are intended to be within the scope of this invention. For example, there may be additionally washing steps, segregation, or isolation steps. Moreover, additional components to vectors, particularly regulatory elements, cells, cell media, etc., which are routine and known in the art can be incorporated herein without deviating from the spirit and scope of the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Mammalian Cells Transfected with a Shuttle Vector Show Expression

A shuttle vector (pPYC-R) was constructed in accordance with the schematic shown in FIG. 1. The sequence is provided in FIG. 2. The vector has an IRES at positions 6001–6505, a GFP at 6506–7258, $Amp^R$ at 9888–655, an *E. coli* replication origin at 656–1456, a yeast 2$\mu$ replication origin at 1461–2808, Trp at 3344–4018 and a CMV promoter at 4853–5614 of SEQ ID NO:1 shown in FIG. 2.

1 $\mu$g of pPYC-R plasmid was transfected into 30% confluent 293 (Phoenix) cells by a standard $Ca^{2+}$ Phosphate transfection method known in the art to test expression of GFP. After incubation for 48 hours in 37° C. $CO_2$ incubator, cells transfected by pPYC-R show green fluorescence color under UV microscope as depicted in FIG. 3.

Example 2

Use of Yeast to Construct Shuttle Vector with Insert, Expression of Insert

This example demonstrates the in-frame fusion of Rip cDNA, an apoptosis-inducing gene when over-expressed in mammalian cells, to a hemagglutinin (HA) tag in pPYC by recombination with non-virus based vector. Rip is further described in Hsu, et al., *Immunity,* 4:387–396 (1996), incorporated herein by reference.

1 $\mu$g of pPYC plasmid (FIGS. 4 and 5) was cut by EcoR I to linearize and was purified from agarose gel. Rip cDNA was amplified by PCR and was purified from agarose gel. The oligo-nucleotide sequences used to amplify Rip were

```
ACGACTCACTATAGGCTAGCCGCCACCATGGCTTACCCATACGATGTTC (SEQ ID NO:3) and
CAGATTACGCTGGGCAACCAGACATGTCCTTGAA

TTGCCAAAAGACGGCAATATGGTGGAAAATAACGTGTCGTACTCTAGAG (SEQ ID NO:4).
GTACCACGCGTGTTAGTTCTGGCTGACGTAAA
```

Flanking sequences required for homologous recombination between PCR fragment and vector are underlined. The purified vector and PCR fragment was co-transfected into yeast by a standard Li/PEG method known in the art. Transformants were plated on SD-W selection plate and were incubated in 30° C. incubator for 4 days. Colonies were harvested and pooled together for plasmid mini-preparation to recover recombinant plasmid from yeast. The plasmid from mini-preparation was transformed into *E. coli* to isolate single colony on LB plus 50 $\mu$g/ml ampicilin. Five colonies were picked to grow up for plasmid mini-preparation and subsequent restriction enzyme digestion and sequencing verification.

Clones with Rip cDNA inserted in-frame downstream of the tag (HA) were co-transfected with pGDB, an apoptosis reporter vector, into 30% confluent mammalian 293 (Phoenix) cells by $Ca^{2+}$ phosphate transfection method to test expression of Rip. FIG. 6 shows the results, extensive cell death due to the expression of HA tagged Rip.

Example 3

Mammalian Cells Transfected with a Shuttle Vector Show Expression

A shuttle vector (pCRU5YMS) was constructed in accordance with the schematic shown in FIG. 7. The sequence is provided in FIG. 8.

One microgram of pCRU5YMS was used to transfect virus packaging cell line Phoenix (293) by a standard $CaPO_4$ transfection method. Under a UV microscope, green fluorescence can be observed after 24 hours, indicating that the GFP has been expressed by pCRU5 promoter. After 48 hours incubation at 30° C., medium containing newly packaged viruses was harvested for a second round of infection of Hela cells. 48 hours after infection, green fluorescence can be observed in most of the Hela cells under the UV microscope as shown in FIG. 9.

We claim:

1. A method for producing an expression shuttle vector comprising a heterologous linear nucleic acid insert and capable of expressing said insert in a mammalian cell, comprising:

(a) transforming yeast with a shuttle vector which shuttle vector comprises:
  (i) an origin of replication functional in yeast;
  (ii) a selectable gene functional in yeast;
  (iii) a promoter functional in a mammalian cell and capable of directing transcription of a polypeptide coding sequence operably linked downstream of said promoter; and
  (iv) an insertion site for an heterologous nucleic acid; wherein said insertion site is an homologous recombination site comprising a first nucleic acid sequence and a second nucleic acid sequence, which first and second nucleic acid sequences are contiguous, and wherein said first and second nucleic acid sequences taken separately correspond to a nucleic acid sequence at the 5' end of said heterologous nucleic acid and a nucleic acid sequence at the 3' end of said heterologous nucleic acid, respectively, and wherein said first and second nucleic acid sequences taken separately comprise nucleic acid sequences of from about 10 to about 100 nucleotides in length;

(b) transforming yeast with a vector comprising an heterologous nucleic acid flanked by said first nucleic acid sequence and said second nucleic acid sequence; and (c) allowing said shuttle vector to recombine so as to insert said heterologous nucleic acid into said shuttle vector at said homologous recombination site.

2. The method according to claim 1, wherein said linear nucleic acid is a PCR product.

3. The method according to claim 2, wherein said PCR product is produced using primers comprising said first nucleic acid sequence, or the complement thereof, and said second nucleic acid sequence, or the complement thereof.

4. A yeast cell comprising an expression shuttle vector, wherein the vector comprises:

(i) an origin of replication functional in yeast;

(ii) a selectable gene functional in yeast;

(iii) a promoter functional in a mammalian cell and capable of directing transcription of a polypeptide coding sequence operably linked downstream of said promoter; and (iv) an insertion site for an heterologous nucleic acid; wherein said insertion site is an homologous recombination site comprising a first nucleic acid sequence and a second nucleic acid sequence, which first and second nucleic acid sequences are contiguous, and wherein said first and second nucleic acid sequences taken separately correspond to a nucleic acid sequence at the 5' end of said heterologous nucleic acid and a nucleic acid sequence at the 3' end of said heterologous nucleic acid, respectively, and wherein said first and second nucleic acid sequences taken separately comprise nucleic acid sequences of from about 10 to about 100 nucleotides in length;

wherein the yeast cell further comprises a vector comprising a heterologous nucleic acid molecule flanked by the first nucleic acid sequence and the second nucleic acid sequence;

such that the shuttle vector recombines to insert the heterologous nucleic acid into the shuttle vector at the homologous recombination site.

* * * * *

UNITED STATES PATENT AND TRADEMARK OFFICE

CERTIFICATE OF CORRECTION

PATENT NO. : 6,645,766 B2
DATED : November 11, 2003
INVENTOR(S) : Ying Luo et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154(b) by 50 days. --.

Signed and Sealed this

Thirtieth Day of August, 2005

JON W. DUDAS
*Director of the United States Patent and Trademark Office*

SEQUENCE LISTING

<160> NUMBER OF SEQ ID NOS: 43

<210> SEQ ID NO 1
<211> LENGTH: 10100
<212> TYPE: DNA
<213> ORGANISM: Artificial Sequence
<220> FEATURE:
<223> OTHER INFORMATION: Description of Artificial Sequence: constructed vectors

<400> SEQUENCE: 1

```
caatgatgag cacttttaaa gttctgctat gtggcgcggt attatcccgt gttgacgccg     60
ggcaagagca actcggtcgc cgcatacact attctcagaa tgacttggtt gagtactcac    120
cagtcacaga aaagcatctt acggatggca tgacagtaag agaattatgc agtgctgcca    180
taaccatgag tgataacact gcggccaact tacttctgac aacgatcgga ggaccgaagg    240
agctaaccgc ttttttgcac aacatggggg atcatgtaac tcgccttgat cgttgggaac    300
cggagctgaa tgaagccata ccaaacgacg agcgtgacac cacgatgcct gtagcaatgg    360
caacaacgtt gcgcaaacta ttaactggcg aactacttac tctagcttcc cggcaacaat    420
taatagactg gatggaggcg gataaagttg caggaccact tctgcgctcg gcccttccgg    480
ctggctggtt tattgctgat aaatctggag ccggtgagcg tgggtctcgc ggtatcattg    540
cagcactggg gccagatggt aagccctccc gtatcgtagt tatctacacg acggggagtc    600
aggcaactat ggatgaacga aatagacaga tcgctgagat aggtgcctca ctgattaagc    660
attggtaact gtcagaccaa gtttactcat atatacttta gattgatttg cggccgcaaa    720
cttcattttt aatttaaaag gatctaggtg aagatccttt ttgataatct catgaccaaa    780
atcccttaac gtgagttttc gttccactga gcgtcagacc ccgtagaaaa gatcaaagga    840
tcttcttgag atcctttttt tctgcgcgta atctgctgct tgcaaacaaa aaaaccaccg    900
ctaccagcgg tggtttgttt gccggatcaa gagctaccaa ctctttttcc gaaggtaact    960
ggcttcagca gagcgcagat accaaatact gtccttctag tgtagccgta gttaggccac   1020
cacttcaaga actctgtagc accgcctaca tacctcgctc tgctaatcct gttaccagtg   1080
gctgctgcca gtggcgataa gtcgtgtctt accgggttgg actcaagacg atagttaccg   1140
gataaggcgc agcggtcggg ctgaacgggg ggttcgtgca cacagcccag cttggagcga   1200
acgacctaca ccgaactgag atacctacag cgtgagctat gagaaagcgc cacgcttccc   1260
gaagggagaa aggcggacag gtatccggta agcggcaggg tcggaacagg agagcgcacg   1320
agggagcttc cagggggaaa cgcctggtat ctttatagtc ctgtcgggtt tcgccacctc   1380
tgacttgagc gtcgattttt gtgatgctcg tcaggggggc ggagcctatg gaaaaacgcc   1440
agcaacgcgg cctttttgct gaacgaagca tctgtgcttc attttgtaga acaaaaatgc   1500
aacgcgagag cgctaatttt tcaaacaaag aatctgagct gcatttttac agaacagaaa   1560
tgcaacgcga aagcgctatt ttaccaacga agaatctgtg cttcattttt gtaaaacaaa   1620
aatgcaacgc gagagcgcta atttttcaaa caaagaatct gagctgcatt tttacagaac   1680
agaaatgcaa cgcgagagcg ctattttacc aacaaagaat ctatacttct tttttgttct   1740
acaaaaatgc atcccgagag cgctattttt ctaacaaagc atcttagatt actttttttc   1800
tcctttgtgc gctctataat gcagtctctt gataactttt tgcactgtag gtccgttaag   1860
gttagaagaa ggctactttg gtgtctattt tctcttccat aaaaaaagcc tgactccact   1920
```

-continued

```
tcccgcgttt actgattact agcgaagctg cgggtgcatt ttttcaagat aaaggcatcc   1980
ccgattatat tctataccga tgtggattgc gcatactttg tgaacagaaa gtgatagcgt   2040
tgatgattct tcattggtca gaaaattatg aacggtttct tctattttgt ctctatatac   2100
tacgtatagg aaatgtttac attttcgtat tgttttcgat tcactctatg aatagttctt   2160
actacaattt ttttgtctaa agagtaatac tagagataaa cataaaaaat gtagaggtcg   2220
agtttagatg caagttcaag gagcgaaagg tggatgggta ggttatatag ggatatagca   2280
cagagatata tagcaaagag atacttttga gcaatgtttg tggaagcggt attcgcaata   2340
ttttagtagc tcgttacagt ccggtgcgtt tttggttttt tgaaagtgcg tcttcagagc   2400
gcttttggtt ttcaaaagcg ctctgaagtt cctatacttt ctagagaata ggaacttcgg   2460
aataggaact tcaaagcgtt tccgaaaacg agcgcttccg aaaatgcaac gcgagctgcg   2520
cacatacagc tcactgttca cgtcgcacct atatctgcgt gttgcctgta tatatatata   2580
catgagaaga acggcatagt gcgtgtttat gcttaaatgc gtacttatat gcgtctattt   2640
atgtaggatg aaaggtagtc tagtacctcc tgtgatatta tcccattcca tgcggggtat   2700
cgtatgcttc cttcagcact accctttagc tgttctatat gctgccactc ctcaattgga   2760
ttagtctcat ccttcaatgc tatcatttcc tttgatattg gatcatatta agaaaccatt   2820
attatcatga cattaaccta taaaaatagg cgtatcacga ggccctttcg tctcgcgcgt   2880
ttcggtgatg acggtgaaaa cctctgacac atgcagctcc cggagacggt cacagcttgt   2940
ctgtaagcgg atgccgggag cagacaagcc cgtcagggcg cgtcagcggg tgttggcggg   3000
tgtcggggct ggcttaacta tgcggcatca gagcagattg tactgagagt gcaccataga   3060
tcaacgacat tactatatat ataatatagg aagcatttaa tagacagcat cgtaatatat   3120
gtgtactttg cagttatgac gccagatggc agtagtggaa gatattcttt attgaaaaat   3180
agcttgtcac cttacgtaca atcttgatcc ggagcttttc tttttttgcc gattaagaat   3240
taattcggtc gaaaaaagaa aaggagaggg ccaagaggga gggcattggt gactattgag   3300
cacgtgagta tacgtgatta agcacacaaa ggcagcttgg agtatgtctg ttattaattt   3360
cacaggtagt tctggtccat tggtgaaagt ttgcggcttg cagagcacag aggccgcaga   3420
atgtgctcta gattccgatg ctgacttgct gggtattata tgtgtgccca atagaaagag   3480
aacaattgac ccggttattg caaggaaaat ttcaagtctt gtaaaagcat ataaaaatag   3540
ttcaggcact ccgaaatact tggttggcgt gtttcgtaat caacctaagg aggatgtttt   3600
ggctctggtc aatgattacg gcattgatat cgtccaactg catggagatg agtcgtggca   3660
agaataccaa gagttcctcg gtttgccagt tattaaaaga ctcgtatttc caaaagactg   3720
caacatacta ctcagtgcag cttcacagaa acctcattcg tttattccct tgtttgattc   3780
agaagcaggt gggacaggtg aacttttgga ttggaactcg atttctgact gggttggaag   3840
gcaagagagc cccgaaagct tacattttat gttagctggt ggactgacgc cagaaaatgt   3900
tggtgatgcg cttagattaa atggcgttat tggtgttgat gtaagcggag gtgtggagac   3960
aaatggtgta aaagactcta acaaaatagc aaatttcgtc aaaaatgcta agaaataggt   4020
tattactgag tagtatttat ttaagtattg tttgtgcact tgccgatcac tatggccatt   4080
taatgtaaat acttaagaaa aaaaaccaaa ttaattttga tacatgctgc atgtgaagac   4140
ccccgctgac gggtagtcaa tcactcagag gagaccctcc caaggcagcg agaccacaag   4200
tcggaaatga aagacccccg ctgacgggta gtcaatcact cagaggagac cctcccaagg   4260
aacagcgaga ccacaagtcg gatgcaactg caagagggtt tattggatac acgggtaccc   4320
```

-continued

```
gggcgactca gtcaatcgga ggactggcgc cccgagtgag ggg ttgtggg ctcttttatt   4380
```

gggcgactca gtcaatcgga ggactggcgc cccgagtgag gggttgtggg ctcttttatt 4380
gagctcgggg agcagaagcg cgcgaacaga agcgagaagc gaactgattg gttagttcaa 4440
ataaggcaca gggtcatttc aggtccttgg ggcaccctgg aaacatctga tggttctcta 4500
gaaactgctg agggctggac cgcatctggg gaccatctgt tcttggccct gagccggggc 4560
aggaactgct taccacagat atcctgtttg gcccatattc agctgttcca tctgttcttg 4620
gccctgagcc ggggcaggaa ctgcttacca cagatatcct gtttggccca tattcagctg 4680
ttccatctgt tcctgacctt gatctgaact tctctattct cagttatgta tttttccatg 4740
ccttgcaaaa tggcgttact taagctagct tgccaaacct acaggtgggg tctttcattc 4800 ccccctttt ctggagacta aataaaatct tttattttat cgtcgatcga ctagatcttc 4860
aatattggcc attagccata ttattcattg gttatatagc ataaatcaat attggctatt 4920
ggccattgca tacgttgtat ctatatcata atatgtacat ttatattggc tcatgtccaa 4980
tatgaccgcc atgttggcat tgattattga ctagttatta atagtaatca attacggggt 5040
cattagttca tagcccatat atggagttcc gcgttacata acttacggta aatggcccgc 5100
ctggctgacc gcccaacgac ccccgcccat tgacgtcaat aatgacgtat gttcccatag 5160
taacgccaat agggactttc cattgacgtc aatgggtgga gtatttacgg taaactgccc 5220
acttggcagt acatcaagtg tatcatatgc caagtccgcc ccctattgac gtcaatgacg 5280
gtaaatggcc cgcctggcat tatgcccagt acatgacctt acgggacttt cctacttggc 5340
agtacatcta cgtattagtc atcgctatta ccatggtgat gcggttttgg cagtacacca 5400
atgggcgtgg atagcggttt gactcacggg gatttccaag tctccacccc attgacgtca 5460
atgggagttt gttttggcac caaaatcaac gggactttcc aaaatgtcgt aacaactgcg 5520
atcgcccgcc ccgttgacgc aaatgggcgg taggcgtgta cggtgggagg tctatataag 5580
cagagctcgt ttagtgaacc gtcagatcac tagaagcttt attgcggtag tttatcacag 5640
ttaaattgct aacgcagtca gtgcttctga cacaacagtc tcgaacttaa gctgcagtga 5700
ctctcttaag gtagccttgc agaagttggt cgtgaggcac tgggcaggta agtatcaagg 5760
ttacaagaca ggtttaagga gaccaataga aactgggctt gtcgagacag agaagactct 5820
tgcgtttctg ataggcacct attggtctta ctgacatcca ctttgccttt ctctccacag 5880
gtgtccactc ccagttcaat tacagctctt aaggctagag tacttaatac gactcactat 5940
aggctagcct cgagccgcca ccatggaatt cacgtgcatg caggccttaa ttaagtcgac 6000
acgttatttt ccaccatatt gccgtctttt ggcaatgtga gggcccggaa acctggccct 6060
gtcttcttga cgagcattcc taggggtctt tcccctctcg ccaaaggaat gcaaggtctg 6120
ttgaatgtcg tgaaggaagc agttcctctg gaagcttctt gaagacaaac aacgtctgta 6180
gcgacccttt gcaggcagcg gaacccccca cctggcgaca ggtgcctctg cggccaaaag 6240
ccacgtgtat aagatacacc tgcaaaggcg gcacaacccc agtgccacgt tgtgagttgg 6300
atagttgtgg aaagagtcaa atggctctcc tcaagcgtat tcaacaaggg gctgaaggat 6360
gcccagaagg taccccattg tatgggatct gatctggggc ctcggtgcac atgctttaca 6420
tgtgtttagt cgaggttaaa aaacgtctag gccccccgaa ccacggggac gtggttttcc 6480
tttgaaaaac acgatgataa tatggggat ccaccggtcg ccaccatggt gagcaagggc 6540
gaggagctgt tcaccggggt ggtgcccatc ctggtcgagc tggacggcga cgtaaacggc 6600
cacaagttca gcgtgtccgg cgagggcgag ggcgatgcca cctacggcaa gctgaccctg 6660

-continued

```
aagttcatct gcaccaccgg caagctgccc gtgccctggc ccaccctcgt gaccaccctg   6720
acctacggcg tgcagtgctt cagccgctac cccgaccaca tgaagcagca cgacttcttc   6780
aagtccgcca tgcccgaagg ctacgtccag gagcgcacca tcttcttcaa ggacgacggc   6840
aactacaaga cccgcgccga ggtgaagttc gagggcgaca ccctggtgaa ccgcatcgag   6900
ctgaagggca tcgacttcaa ggaggacggc aacatcctgg ggcacaagct ggagtacaac   6960
tacaacagcc acaacgtcta tatcatggcc gacaagcaga agaacggcat caaggtgaac   7020
ttcaagatcc gccacaacat cgaggacggc agcgtgcagc tcgccgacca ctaccagcag   7080
aacaccccca tcggcgacgg ccccgtgctg ctgcccgaca accactacct gagcacccag   7140
tccgccctga gcaaagaccc caacgagaag cgcgatcaca tggtcctgct ggagttcgtg   7200
accgccgccg ggatcactct cggcatggac gagctgtaca agtaaagcgg ccgctcgacg   7260
ataaattccc tttagtgagg gttaatgctt cgagcagaca tgataagata cattgatgag   7320
tttggacaaa ccacaactag aatgcagtga aaaaaatgct ctatttgtga aatttgtgat   7380
gctattgctg tatttgtaac cattataagc tgcaataaac aagttaacaa caacaattgc   7440
attcatttta tgtttcaggt tcagggggag atgtgggagg ttttttaaag caagtaaaac   7500
ctctacaaat gtggtaaaat ccgataagga tccggcagtc tagaggatgg tccacccccg   7560
gggtcggcag ccttcacgtg ggcggcgtgt atccaagctg cgatgccgtc tactttgagg   7620
gcggtggggg tggtcagcag gactgtgtaa ggtcctttcc agcgaggttc taggttctta   7680
gtctggtgtc ggcggaccca cactgtgtcg ccgactcggt aagggtgagg taccaccggt   7740
cggtccagtt gttcttggta cgtgccgcca gaggtctcca gacttcgtgc tggactaagt   7800
agagagcctg taagtgagct tggagagagg ggctgttagt aactcttgtc atgtcagggt   7860
cagggaagtt tacaaggggc gggggtgccc catataagat ctcatatggc catatggggg   7920
cgcctagaga aggagtgagg gctggataaa gggaggatcg aggcggggtc gaacgaggag   7980
gttcaagggg gagagacggg gcggatggag gaagaggagg cggaggctta gggtgtacaa   8040
agggcttgac ccagggaggg gggtcaaaag ccaaggcttc ccaggtcacg atgtagggga   8100
cctggtctgg gtgtccatgc gggccaggtg aaaagacctt gatcttaacc tgggtgatga   8160
ggtctcggtt aaaggtgccg tctcgcggcc atccgacgtt aaaggttggc cattctgcag   8220
agcagaaggt aacccaacgt ctcttcttga catctaccga ctggttgtga gcgatccgct   8280
cgacatcttt ccagtgacct aaggtcaaac ttaagggagt ggtaacagtc tggcccgggc   8340
ccatattttc agacaaatac agaaacacag tcagacagag acaacacaga acgatgctgc   8400
agcagacaag acgcgcggcg cggcttcggt cccaaaccga aagcaaaaat tcagacggag   8460
gcgggaactg ttttaggttc tcgtctccta ccagaaccac atatccctcc tctaaggggg   8520
gtgcaccaaa gagtccaaaa cgatcgggat tttggactc aggtcgggcc acaaaaacgg   8580
cccccgaagt ccctgggacg tctcccaggg ttgcggccgg gtgttccgaa ctcgtcagtt   8640
ccaccacggg tccgccagat acagagctag ttagctaact agtaccgacg caggcgcata   8700
aaatcagtca tagacactag acaatcggac agacacagat aagttgctgg ccagcttacc   8760
tcccggtggt gggtcggtgg tccctgggca ggggtctccc gatcccggac gagcccccaa   8820
atgaaagacc cccgctgacg ggtagtcaat cactcagagg agaccctccc aaggaacagc   8880
gagaccacaa gtcggatgca actgcaagag ggtttattgg atacacgggt acccgggcga   8940
ctcagtcaat cggaggactg gcgccccgag tgaggggttg tgggctcttt tattgagctc   9000
ggggagcaga agcgcgcgaa cagaagcgag aagcgaactg attggttagt tcaaataagg   9060
```

```
cacagggtca tttcaggtcc ttggggcacc ctggaaacat ctgatggttc tctagaaact   9120
gctgagggct ggaccgcatc tggggaccat ctgttcttgg ccctgagccg gggcaggaac   9180
tgcttaccac agatatcctg tttggcccat attcagctgt tccatctgtt cttggccctg   9240
agccggggca ggaactgctt accacagata tccgctttgg cccatattca gctgttccat   9300
ctgttcctga ccttgatctg aacttttcta ttctcagtta tgtatttttc catgccttgc   9360
aaaatggcgt tacttaagct agcttgccaa acctacaggt ggggtctttc acatgtatat   9420
gtcaaaaata aaaatcaact aattgactag taattaatat gactggcata atgggaaatt   9480
gatcctgaca gatgcaaact ggcttctcag cagcgcattt atgttgtcaa ctgaggaagg   9540
aaacgttaat gacagaaact ctaagtaatt tccacgttta tctattttta tttatactag   9600
ctttggtaac aggaatattg cagcattcat gcacattgaa acccttatga aataaaaaca   9660
tctgtgcatt taaaatggaa ttaacatttt aaatgttaaa aaaagctggc ttagcttccc   9720
cccgcccccct agggcataga acaagtcaaa tgctttatat atttgagttt gggatgtatt   9780
aggaaactcc taagagcaaa gctgttcttg aagacgaaag ggcctcgtga tacgcctatt   9840
tttataggtt aatgtcatga gacaataacc ctgataaatg cttcaataat attgaaaaag   9900
gaagagtatg agtattcaac atttccgtgt cgcccttatt ccctttttttg cggcattttg   9960
ccttcctgtt tttgctcacc cagaaacgct ggtgaaagta aaagatgctg aagatcagtt  10020
gggtgcacga gtgggttaca tcgaactgga tctcaacagc ggtaagatcc ttgagagttt  10080
tcgccccgaa gaacgttttc                                              10100
```

<210> SEQ ID NO 2
<211> LENGTH: 9687
<212> TYPE: DNA
<213> ORGANISM: Artificial Sequence
<220> FEATURE:
<223> OTHER INFORMATION: Description of Artificial Sequence: constructed vectors

<400> SEQUENCE: 2

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
```

-continued

```
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cgccaccatg gcttacccat acgatgttcc agattacgct gggcaaccag   1140
acatgtcctt gaatgtcatt aagatgaaat ccagtgactt cctggagagt gcagaactgg   1200
acagcggagg ctttgggaag gtgtctctgt gtttccacag aacccaggga ctcatgatca   1260
tgaaaacagt gtacaagggg cccaactgca ttgagcacaa cgaggccctc ttggaggagg   1320
cgaagatgat gaacagactg agacacagcc gggtggtgaa gctcctgggc gtcatcatag   1380
aggaagggaa gtactccctg gtgatggagt acatggagaa gggcaacctg atgcacgtgc   1440
tgaaagccga gatgagtact ccgctttctg taaaaggaag gataatttgg gaaatcattg   1500
aaggaatgtg ctacttacat gaaaaggcgt gatacacaag gacctgaagc ctgaaaatat   1560
ccttgttgat aatgacttcc acattaagat cgcagacctc ggccttgcct cctttaagat   1620
gtggagcaaa ctgaataatg aagagcacaa tgagctgagg gaagtggacg gcaccgctaa   1680
gaagaatggc ggcaccctct actacatggc gcccgagcac ctgaatgacg tcaacgcaaa   1740
gcccacagag aagtcggatg tgtacagctt tgctgtagta ctctgggcga tatttgcaaa   1800
taaggagcca tatgaaaatg ctatctgtga gcagcagttg ataatgtgca taaaatctgg   1860
gaacaggcca gatgtggatg acatcactga gtactgccca agagaaatta tcagtctcat   1920
gaagctctgc tgggaagcga atccggaagc tcggccgaca tttcctggca ttgaagaaaa   1980
atttaggcct ttttatttaa gtcaattaga agaaagtgta gaagaggacg tgaagagttt   2040
aaagaaagag tattcaaacg aaaatgcagt tgtgaagaga atgcagtctc ttcaacttga   2100
ttgtgtggca gtaccttcaa gccggtcaaa ttcagccaca gaacagcctg gttcactgca   2160
cagttcccag ggacttggga tgggtcctgt ggaggagtcc tggtttgctc cttccctgga   2220
gcacccacaa gaagagaatg agcccagcct gcagagtaaa ctccaagacg aagccaacta   2280
ccatctttat ggcagccgca tggacaggca gacgaaacag cagcccagac agaatgtggc   2340
ttacaacaga gaggaggaaa ggagacgcag ggtctcccat gacccttttg cacagcaaag   2400
accttacgag aattttcaga atacagaggg aaaaggcact gtttattcca gtgcagccag   2460
tcatggtaat gcagtgcacc agccctcagg gctcaccagc caacctcaag tactgtatca   2520
gaacaatgga ttatatagct cacatggctt tggaacaaga ccactggatc caggaacagc   2580
aggtcccaga gtttggtaca ggccaattcc aagtcatatg cctagtctgc ataatatccc   2640
agtgcctgag accaactatc taggaaatac acccaccatg ccattcagct ccttgccacc   2700
aacagatgaa tctataaaat ataccatata caatagtact ggcattcaga ttggagccta   2760
caattatatg gagattggtg ggacgagttc atcactacta gacagcacaa atacgaactt   2820
caaagaagag ccagctgcta agtaccaagc tatctttgat aataccacta gtctgacgga   2880
taaacacctg gacccaatca gggaaaatct gggaaagcac tggaaaaact gtgcccgtaa   2940
actgggcttc acacagtctc agattgatga aattgaccat gactatgagc gagatggact   3000
gaaagaaaag gtttaccaga tgctccaaaa gtgggtgatg agggaaggca taaagggagc   3060
cacggtgggg aagctggccc aggcgctcca ccagtgttcc aggatcgacc ttctgagcag   3120
cttgatttac gtcagccaga actaacacgc gtggtacctc tagagtcgac acgttatttt   3180
ccaccatatt gccgtctttt ggcaatgtga gggcccggaa acctggccct gtcttcttga   3240
cgagcattcc taggggtctt tcccctctcg ccaaaggaat gcaaggtctg ttgaatgtcg   3300
```

-continued

```
tgaaggaagc agttcctctg gaagcttctt gaagacaaac aacgtctgta gcgacccttt   3360
gcaggcagcg gaacccccca cctggcgaca ggtgcctctg cggccaaaag ccacgtgtat   3420
aagatacacc tgcaaaggcg gcacaacccc agtgccacgt tgtgagttgg atagttgtgg   3480
aaagagtcaa atggctctcc tcaagcgtat tcaacaaggg gctgaaggat gcccagaagg   3540
taccccattg tatgggatct gatctggggc ctcggtgcac atgctttaca tgtgtttagt   3600
cgaggttaaa aaacgtctag gccccccgaa ccacggggac gtggttttcc tttgaaaaac   3660
acgatgataa tatgggggat ccaccggtcg ccaccatggt gagcaagggc gaggagctgt   3720
tcaccggggt ggtgcccatc ctggtcgagc tggacggcga cgtaaacggc cacaagttca   3780
gcgtgtccgg cgagggcgag ggcgatgcca cctacggcaa gctgaccctg aagttcatct   3840
gcaccaccgg caagctgccc gtgccctggc ccaccctcgt gaccaccctg acctacggcg   3900
tgcagtgctt cagccgctac cccgaccaca tgaagcagca cgacttcttc aagtccgcca   3960
tgcccgaagg ctacgtccag gagcgcacca tcttcttcaa ggacgacggc aactacaaga   4020
cccgcgccga ggtgaagttc gagggcgaca ccctggtgaa ccgcatcgag ctgaagggca   4080
tcgacttcaa ggaggacggc aacatcctgg ggcacaagct ggagtacaac tacaacagcc   4140
acaacgtcta tatcatggcc gacaagcaga agaacggcat caaggtgaac ttcaagatcc   4200
gccacaacat cgaggacggc agcgtgcagc tcgccgacca ctaccagcag aacaccccca   4260
tcggcgacgg ccccgtgctg ctgcccgaca accactacct gagcacccag tccgccctga   4320
gcaaagaccc caacgagaag cgcgatcaca tggtcctgct ggagttcgtg accgccgccg   4380
ggatcactct cggcatggac gagctgtaca agtaaagcgg ccgcttccct ttagtgaggg   4440
ttaatgcttc gagcagacat gataagatac attgatgagt ttggacaaac cacaactaga   4500
atgcagtgaa aaaaatgctt tatttgtgaa atttgtgatg ctattgcttt atttgtaacc   4560
attataagct gcaataaaca agttaacaac aacaattgca ttcattttat gtttcaggtt   4620
cagggggaga tgtgggaggt tttttaaagc aagtaaaacc tctacaaatg tggtaaaatc   4680
cgataaggat cgatccgggc tggcgtaata gcgaagaggc ccgcaccgat cgcccttccc   4740
aacagttgcg cagcctgaat ggcgaatgga cgcgccctgt agcggcgcat taagcgcggc   4800
gggtgtggtg gttacgcgca gcgtgaccgc tacacttgcc agcgccctag cgcccgctcc   4860
tttcgctttc ttcccttcct ttctcgccac gttcgccggc tttccccgtc aagctctaaa   4920
tcgggggctc cctttagggt tccgatttag agctttacgg cacctcgacc gcaaaaaact   4980
tgatttgggt gatgctcgaa cgaagcatct gtgcttcatt ttgtagaaca aaaatgcaac   5040
gcgagagcgc taatttttca aacaaagaat ctgagctgca tttttacaga acagaaatgc   5100
aacgcgaaag cgctatttta ccaacgaaga atctgtgctt catttttgta aaacaaaaat   5160
gcaacgcgag agcgctaatt tttcaaacaa agaatctgag ctgcattttt acagaacaga   5220
aatgcaacgc gagagcgcta ttttaccaac aaagaatcta tacttctttt ttgttctaca   5280
aaaatgcatc ccgagagcgc tatttttcta acaaagcatc ttagattact ttttttctcc   5340
tttgtgcgct ctataatgca gtctcttgat aactttttgc actgtaggtc cgttaaggtt   5400
agaagaaggc tactttggtg tctattttct cttccataaa aaaagcctga ctccacttcc   5460
cgcgtttact gattactagc gaagctgcgg gtgcattttt tcaagataaa ggcatccccg   5520
attatattct ataccgatgt ggattgcgca tactttgtga acagaaagtg atagcgttga   5580
tgattcttca ttggtcagaa aattatgaac ggtttcttct attttgtctc tatatactac   5640
gtataggaaa tgtttacatt ttcgtattgt tttcgattca ctctatgaat agttcttact   5700
```

-continued

```
acaatttttt tgtctaaaga gtaatactag agataaacat aaaaaatgta gaggtcgagt   5760
ttagatgcaa gttcaaggag cgaaaggtgg atgggtaggt tatataggga tatagcacag   5820
agatatatag caaagagata cttttgagca atgtttgtgg aagcggtatt cgcaatattt   5880
tagtagctcg ttacagtccg gtgcgttttt ggttttttga aagtgcgtct tcagagcgct   5940
tttggttttc aaaagcgctc tgaagttcct atactttcta gagaatagga acttcggaat   6000
aggaacttca aagcgtttcc gaaaacgagc gcttccgaaa atgcaacgcg agctgcgcac   6060
atacagctca ctgttcacgt cgcacctata tctgcgtgtt gcctgtatat atatatacat   6120
gagaagaacg gcatagtgcg tgtttatgct taaatgcgta cttatatgcg tctatttatg   6180
taggatgaaa ggtagtctag tacctcctgt gatattatcc cattccatgc ggggtatcgt   6240
atgcttcctt cagcactacc ctttagctgt tctatatgct gccactcctc aattggatta   6300
gtctcatcct tcaatgctat catttccttt gatattggat catattaaga aaccattatt   6360
atcatgacat taacctataa aaataggcgt atcacgaggc cctttcgtct cgcgcgtttc   6420
ggtgatgacg gtgaaaacct ctgacacatg cagctcccgg agacggtcac agcttgtctg   6480
taagcggatg ccgggagcag acaagcccgt cagggcgcgt cagcgggtgt tggcgggtgt   6540
cggggctggc ttaactatgc ggcatcagag cagattgtac tgagagtgca ccatagatca   6600
acgacattac tatatatata atataggaag catttaatag acagcatcgt aatatatgtg   6660
tactttgcag ttatgacgcc agatggcagt agtggaagat attctttatt gaaaaatagc   6720
ttgtcacctt acgtacaatc ttgatccgga gcttttcttt ttttgccgat taagaattaa   6780
ttcggtcgaa aaaagaaaag gagagggcca agagggaggg cattggtgac tattgagcac   6840
gtgagtatac gtgattaagc acacaaaggc agcttggagt atgtctgtta ttaatttcac   6900
aggtagttct ggtccattgg tgaaagtttg cggcttgcag agcacagagg ccgcagaatg   6960
tgctctagat tccgatgctg acttgctggg tattatatgt gtgcccaata gaaagagaac   7020
aattgacccg gttattgcaa ggaaaatttc aagtcttgta aaagcatata aaaatagttc   7080
aggcactccg aaatacttgg ttggcgtgtt tcgtaatcaa cctaaggagg atgttttggc   7140
tctggtcaat gattacggca ttgatatcgt ccaactgcat ggagatgagt cgtggcaaga   7200
ataccaagag ttcctcggtt tgccagttat taaaagactc gtatttccaa aagactgcaa   7260
catactactc agtgcagctt cacagaaacc tcattcgttt attcccttgt ttgattcaga   7320
agcaggtggg acaggtgaac ttttggattg gaactcgatt tctgactggg ttggaaggca   7380
agagagcccc gaaagcttac attttatgtt agctggtgga ctgacgccag aaaatgttgg   7440
tgatgcgctt agattaaatg gcgttattgg tgttgatgta agcggaggtg tggagacaaa   7500
tggtgtaaaa gactctaaca aaatagcaaa tttcgtcaaa aatgctaaga aataggttat   7560
tactgagtag tatttattta agtattgttt gtgcacttgc cgatcgcgta tggtgcactc   7620
tcagtacaat ctgctctgat gccgcatagt taagccagcc ccgacacccg ccaacacccg   7680
ctgacgcgcc ctgacgggct tgtctgctcc cggcatccgc ttacagacaa gctgtgaccg   7740
tctccgggag ctgcatgtgt cagaggtttt caccgtcatc accgaaacgc gcgagacgaa   7800
agggcctcgt gatacgccta tttttatagg ttaatgtcat gataataatg gtttcttaga   7860
cgtcaggtgg cacttttcgg ggaaatgtgc gcggaacccc tatttgttta tttttctaaa   7920
tacattcaaa tatgtatccg ctcatgagac aataaccctg ataaatgctt caataatatt   7980
gaaaaaggaa gagtatgagt attcaacatt tccgtgtcgc ccttattccc ttttttgcgg   8040
```

-continued

```
cattttgcct tcctgttttt gctcacccag aaacgctggt gaaagtaaaa gatgctgaag   8100

atcagttggg tgcacgagtg ggttacatcg aactggatct caacagcggt aagatccttg   8160

agagttttcg ccccgaagaa cgttttccaa tgatgagcac ttttaaagtt ctgctatgtg   8220

gcgcggtatt atcccgtatt gacgccgggc aagagcaact cggtcgccgc atacactatt   8280

ctcagaatga cttggttgag tactcaccag tcacagaaaa gcatcttacg gatggcatga   8340

cagtaagaga attatgcagt gctgccataa ccatgagtga taacactgcg gccaacttac   8400

ttctgacaac gatcggagga ccgaaggagc taaccgcttt tttgcacaac atgggggatc   8460

atgtaactcg ccttgatcgt tgggaaccgg agctgaatga agccatacca aacgacgagc   8520

gtgacaccac gatgcctgta gcaatggcaa caacgttgcg caaactatta actggcgaac   8580

tacttactct agcttcccgg caacaattaa tagactggat ggaggcggat aaagttgcag   8640

gaccacttct gcgctcggcc cttccggctg gctggtttat tgctgataaa tctggagccg   8700

gtgagcgtgg gtctcgcggt atcattgcag cactggggcc agatggtaag ccctcccgta   8760

tcgtagttat ctacacgacg gggagtcagg caactatgga tgaacgaaat agacagatcg   8820

ctgagatagg tgcctcactg attaagcatt ggtaactgtc agaccaagtt tactcatata   8880

tactttagat tgatttaaaa cttcattttt aatttaaaag gatctaggtg aagatccttt   8940

ttgataatct catgaccaaa atcccttaac gtgagttttc gttccactga gcgtcagacc   9000

ccgtagaaaa gatcaaagga tcttcttgag atcctttttt tctgcgcgta atctgctgct   9060

tgcaaacaaa aaaaccaccg ctaccagcgg tggtttgttt gccggatcaa gagctaccaa   9120

ctctttttcc gaaggtaact ggcttcagca gagcgcagat accaaatact gtccttctag   9180

tgtagccgta gttaggccac cacttcaaga actctgtagc accgcctaca tacctcgctc   9240

tgctaatcct gttaccagtg gctgctgcca gtggcgataa gtcgtgtctt accgggttgg   9300

actcaagacg atagttaccg gataaggcgc agcggtcggg ctgaacgggg ggttcgtgca   9360

cacagcccag cttggagcga acgacctaca ccgaactgag atacctacag cgtgagctat   9420

gagaaagcgc cacgcttccc gaagggagaa aggcggacag gtatccggta agcggcaggg   9480

tcggaacagg agagcgcacg agggagcttc caggggggaaa cgcctggtat ctttatagtc   9540

ctgtcgggtt tcgccacctc tgacttgagc gtcgattttt gtgatgctcg tcaggggggc   9600

ggagcctatg gaaaaacgcc agcaacgcgg cctttttacg gttcctggcc ttttgctggc   9660

cttttgctca catggctcga cagatct                                       9687
```

<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: PCR primer for RID

<400> SEQUENCE: 3

```
acgactcact ataggctagc cgccaccatg gcttacccat acgatgttcc agattacgct     60

gggcaaccag acatgtcctt gaa                                              83
```

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: PCR primer for RID -continued

<400> SEQUENCE: 4
ttgccaaaag acggcaatat ggtggaaaat aacgtgtcga ctctagaggt accacgcgtg 60
ttagttctgg ctgacgtaaa 80

<210> SEQ ID NO 5
<211> LENGTH: 8614
<212> TYPE: DNA
<213> ORGANISM: Artificial Sequence
<220> FEATURE:
<223> OTHER INFORMATION: Description of Artificial Sequence: constructed vectors

<400> SEQUENCE: 5
atcacgaggc cctttcgtct tcaagaacag ctttgctctt aggagtttcc taatacatcc 60
caaactcaaa tatataaagc atttgacttg ttctatgccc tagttattaa tagtaatcaa 120
ttacggggtc attagttcat agcccatata tggagttccg cgttacataa cttacggtaa 180
atggcccgcc tggctgaccg cccaacgacc cccgcccatt gacgtcaata atgacgtatg 240
ttcccatagt aacgccaata gggactttcc attgacgtca atgggtggag tatttacggt 300
aaactgccca cttggcagta catcaagtgt atcatatgcc aagtacgccc cctattgacg 360
tcaatgacgg taaatggccc gcctggcatt atgcccagta catgacctta tgggactttc 420
ctacttggca gtacatctac gtattagtca tcgctattac catggtgatg cggttttggc 480
agtacatcaa tgggcgtgga tagcggtttg actcacgggg atttccaagt ctccacccca 540
ttgacgtcaa tgggagtttg ttttggcacc aaaatcaacg ggactttcca aaatgtcgta 600
acaactccgc cccattgacg caaatgggcg gtaggcatgt acggtgggag gtctatataa 660
gcagagctca ataaaagagc ccacaacccc tcactcgggg cgccagtcct ccgattgact 720
gagtcgcccg ggtacccgtg tatccaataa accctcttgc agttgcatcc gacttgtggt 780
ctcgctgttc cttgggaggg tctcctctga gtgattgact acccgtcagc gggggtcttt 840
catttggggg ctcgtccggg atcgggagac ccctgcccag ggaccaccga cccaccaccg 900
ggaggtaagc tggccagcaa cttatctgtg tctgtccgat tgtctagtgt ctatgactga 960
ttttatgcgc ctgcgtcggt actagttagc taactagctc tgtatctggc ggacccgtgg 1020
tggaactgac gagttcggaa cacccggccg caaccctggg agacgtccca gggacttcgg 1080
gggccgtttt tgtggcccga cctgagtcca aaaatcccga tcgttttgga ctctttggtg 1140
cacccccctt agaggaggga tatgtggttc tggtaggaga cgagaaccta aaacagttcc 1200
cgcctccgtc tgaatttttg ctttcggttt gggaccgaag ccgcgccgcg cgtcttgtct 1260
gctgcagcat cgttctgtgt tgtctctgtc tgactgtgtt tctgtatttg tctgaaaata 1320
tcggcccggg ccagactgtt accactccct taagtttgac cttaggtcac tggaaagatg 1380
tcgagcggat cgctcacaac cagtcggtag atgtcaagaa gagacgttgg gttaccttct 1440
gctctgcaga atggccaacc tttaacgtcg gatggccgcg agacggcacc tttaaccgag 1500
acctcatcac ccaggttaag atcaaggtct tttcacctgg cccgcatgga cacccagacc 1560
aggtccccta catcgtgacc tgggaagcct tggcttttga cccccctccc tgggtcaagc 1620
cctttgtaca ccctaagcct ccgcctcctc ttcctccatc cgccccgtct ctcccccttg 1680
aacctcctcg ttcgaccccg cctcgatcct ccctttatcc agccctcact ccttctctag 1740
gcgcccccat atggccatat gagatcttat atggggcacc cccgcccctt gtaaacttcc 1800
ctgaccctga catgacaaga gttactaaca gcccctctct ccaagctcac ttacaggctc 1860

-continued

```
tctacttagt ccagcacgaa gtctggagac ctctggcggc agcctaccaa gaacaactgg   1920
accgaccggt ggtacctcac ccttaccgag tcggcgacac agtgtgggtc cgccgacacc   1980
agactaagaa cctagaacct cgctggaaag gaccttacac agtcctgctg accaccccca   2040
ccgccctcaa agtagacggc atcgcagctt ggatacacgc cgcccacgtg aaggctgccg   2100
accccggggg tggaccatcc tctagactgc cggatctcga gggatccacc accatggacc   2160
cccattaaat tggaattcct gcagcccggg ggatccacta gttctagagc gaattaattc   2220
cggttatttt ccaccatatt gccgtctttt ggcaatgtga gggcccggaa acctggccct   2280
gtcttcttga cgagcattcc taggggtctt tcccctctcg ccaaaggaat gcaaggtctg   2340
ttgaatgtcg tgaaggaagc agttcctctg gaagcttctt gaagacaaac aacgtctgta   2400
gcgacccttt gcaggcagcg gaacccccca cctggcgaca ggtgcctctg cggccaaaag   2460
ccacgtgtat aagatacacc tgcaaaggcg gcacaacccc agtgccacgt tgtgagttgg   2520
atagttgtgg aaagagtcaa atggctctcc tcaagcgtat tcaacaaggg gctgaaggat   2580
gcccagaagg taccccattg tatgggatct gatctggggc ctcggtgcac atgctttaca   2640
tgtgtttagt cgaggttaaa aaacgtctag gccccccgaa ccacggggac gtggttttcc   2700
tttgaaaaac acgatgataa tatgggggat ccaccggtcg ccaccatggt gagcaagggc   2760
gaggagctgt tcaccggggt ggtgcccatc ctggtcgagc tggacggcga cgtaaacggc   2820
cacaagttca gcgtgtccgg cgagggcgag ggcgatgcca cctacggcaa gctgaccctg   2880
aagttcatct gcaccaccgg caagctgccc gtgccctggc ccaccctcgt gaccaccctg   2940
acctacggcg tgcagtgctt cagccgctac cccgaccaca tgaagcagca cgacttcttc   3000
aagtccgcca tgcccgaagg ctacgtccag gagcgcacca tcttcttcaa ggacgacggc   3060
aactacaaga cccgcgccga ggtgaagttc gagggcgaca ccctggtgaa ccgcatcgag   3120
ctgaagggca tcgacttcaa ggaggacggc aacatcctgg ggcacaagct ggagtacaac   3180
tacaacagcc acaacgtcta tatcatggcc gacaagcaga agaacggcat caaggtgaac   3240
ttcaagatcc gccacaacat cgaggacggc agcgtgcagc tcgccgacca ctaccagcag   3300
aacaccccca tcggcgacgg ccccgtgctg ctgcccgaca accactacct gagcacccag   3360
tccgccctga gcaaagaccc caacgagaag cgcgatcaca tggtcctgct ggagttcgtg   3420
accgccgccg ggatcactct cggcatggac gagctgtaca agtaaagcgg ccgctcgacg   3480
ataaaataaa agattttatt tagtctccag aaaaaggggg gaatgaaaga ccccacctgt   3540
aggtttggca agctagctta agtaacgcca ttttgcaagg catggaaaaa tacataactg   3600
agaatagaga agttcagatc aaggtcagga acagatggaa cagctgaata tgggccaaac   3660
aggatatctg tggtaagcag ttcctgcccc ggctcagggc caagaacaga tggaacagct   3720
gaatatgggc caaacaggat atctgtggta agcagttcct gccccggctc agggccaaga   3780
acagatggtc cccagatgcg gtccagccct cagcagtttc tagagaacca tcagatgttt   3840
ccagggtgcc ccaaggacct gaaatgaccc tgtgccttat ttgaactaac caatcagttc   3900
gcttctcgct tctgttcgcg cgcttctgct ccccgagctc aataaaagag cccacaaccc   3960
ctcactcggg gcgccagtcc tccgattgac tgagtcgccc gggtacccgt gtatccaata   4020
aaccctcttg cagttgcatc cgacttgtgg tctcgctgtt ccttgggagg gtctcctctg   4080
agtgattgac tacccgtcag cgggggtctt tcatttccga cttgtggtct cgctgccttg   4140
ggagggtctc ctctgagtga ttgactaccc gtcagcgggg gtcttcacat gcagcatgta   4200
```

-continued

```
tcaaaattaa tttggttttt tttcttaagt atttacatta aatggccata gtgatcggca   4260
agtgcacaaa caatacttaa ataaatacta ctcagtaata acctatttct tagcattttt   4320
gacgaaattt gctattttgt tagagtcttt tacaccattt gtctccacac ctccgcttac   4380
atcaacacca ataacgccat ttaatctaag cgcatcacca acattttctg gcgtcagtcc   4440
accagctaac ataaaatgta agctttcggg gctctcttgc cttccaaccc agtcagaaat   4500
cgagttccaa tccaaaagtt cacctgtccc acctgcttct gaatcaaaca agggaataaa   4560
cgaatgaggt ttctgtgaag ctgcactgag tagtatgttg cagtcttttg gaaatacgag   4620
tcttttaata actggcaaac cgaggaactc ttggtattct tgccacgact catctccatg   4680
cagttggacg atatcaatgc cgtaatcatt gaccagagcc aaaacatcct ccttaggttg   4740
attacgaaac acgccaacca agtatttcgg agtgcctgaa ctatttttat atgcttttac   4800
aagacttgaa attttccttg caataaccgg gtcaattgtt ctctttctat tgggcacaca   4860
tataataccc agcaagtcag catcggaatc tagagcacat tctgcggcct ctgtgctctg   4920
caagccgcaa actttcacca atggaccaga actacctgtg aaattaataa cagacatact   4980
ccaagctgcc tttgtgtgct taatcacgta tactcacgtg ctcaatagtc accaatgccc   5040
tccctcttgg ccctctcctt ttcttttttc gaccgaatta attcttaatc ggcaaaaaaa   5100
gaaaagctcc ggatcaagat tgtacgtaag gtgacaagct atttttcaat aaagaatatc   5160
ttccactact gccatctggc gtcataactg caaagtacac atatattacg atgctgtcta   5220
ttaaatgctt cctatattat atatatagta atgtcgttga tctatggtgc actctcagta   5280
caatctgctc tgatgccgca tagttaagcc agccccgaca cccgccaaca cccgctgacg   5340
cgccctgacg ggcttgtctg ctcccggcat ccgcttacag acaagctgtg accgtctccg   5400
ggagctgcat gtgtcagagg ttttcaccgt catcaccgaa acgcgcgaga cgaaagggcc   5460
tcgtgatacg cctattttta taggttaatg tcatgataat aatggtttct taatatgatc   5520
caatatcaaa ggaaatgata gcattgaagg atgagactaa tccaattgag gagtggcagc   5580
atatagaaca gctaaagggt agtgctgaag gaagcatacg ataccccgca tggaatggga   5640
taatatcaca ggaggtacta gactaccttt catcctacat aaatagacgc atataagtac   5700
gcatttaagc ataaacacgc actatgccgt tcttctcatg tatatatata tacaggcaac   5760
acgcagatat aggtgcgacg tgaacagtga gctgtatgtg cgcagctcgc gttgcatttt   5820
cggaagcgct cgttttcgga aacgctttga agttcctatt ccgaagttcc tattctctag   5880
aaagtatagg aacttcagag cgcttttgaa aaccaaaagc gctctgaaga cgcactttca   5940
aaaaaccaaa aacgcaccgg actgtaacga gctactaaaa tattgcgaat accgcttcca   6000
caaacattgc tcaaaagtat ctctttgcta tatatctctg tgctatatcc ctatataacc   6060
tacccatcca cctttcgctc cttgaacttg catctaaact cgacctctac atttttttatg   6120
tttatctcta gtattactct ttagacaaaa aaattgtagt aagaactatt catagagtga   6180
atcgaaaaca atacgaaaat gtaaacattt cctatacgta gtatatagag acaaaataga   6240
agaaaccgtt cataattttc tgaccaatga agaatcatca acgctatcac tttctgttca   6300
caaagtatgc gcaatccaca tcggtataga atataatcgg ggatgccttt atcttgaaaa   6360
aatgcacccg cagcttcgct agtaatcagt aaacgcggga agtggagtca ggcttttttt   6420
atggaagaga aaatagacac caaagtagcc ttcttctaac cttaacggac ctacagtgca   6480
aaaagttatc aagagactgc attatagagc gcacaaagga gaaaaaaagt aatctaagat   6540
gctttgttag aaaaatagcg ctctcgggat gcatttttgt agaacaaaaa agaagtatag   6600
```

```
attctttgtt ggtaaaatag cgctctcgcg ttgcatttct gttctgtaaa aatgcagctc   6660

agattctttg tttgaaaaat tagcgctctc gcgttgcatt tttgttttac aaaaatgaag   6720

cacagattct tcgttggtaa aatagcgctt tcgcgttgca tttctgttct gtaaaaatgc   6780

agctcagatt ctttgtttga aaaattagcg ctctcgcgtt gcatttttgt tctacaaaat   6840

gaagcacaga tgcttcgttc gagcaaaagg ccagcaaaag gccaggaacc gtaaaaaggc   6900

cgcgttgctg gcgtttttcc ataggctccg cccccctgac gagcatcaca aaaatcgacg   6960

ctcaagtcag aggtggcgaa acccgacagg actataaaga taccaggcgt ttccccctgg   7020

aagctccctc gtgcgctctc ctgttccgac cctgccgctt accggatacc tgtccgcctt   7080

tctcccttcg ggaagcgtgg cgctttctca tagctcacgc tgtaggtatc tcagttcggt   7140

gtaggtcgtt cgctccaagc tgggctgtgt gcacgaaccc cccgttcagc ccgaccgctg   7200

cgccttatcc ggtaactatc gtcttgagtc caacccggta agacacgact tatcgccact   7260

ggcagcagcc actggtaaca ggattagcag agcgaggtat gtaggcggtg ctacagagtt   7320

cttgaagtgg tggcctaact acggctacac tagaaggaca gtatttggta tctgcgctct   7380

gctgaagcca gttaccttcg gaaaaagagt tggtagctct tgatccggca aacaaaccac   7440

cgctggtagc ggtggttttt ttgtttgcaa gcagcagatt acgcgcagaa aaaaaggatc   7500

tcaagaagat cctttgatct tttctacggg gtctgacgct cagtggaacg aaaactcacg   7560

ttaagggatt ttggtcatga gattatcaaa aaggatcttc acctagatcc ttttaaatta   7620

aaaatgaagt ttgcgcaaat caatctaaag tatatatgag taaacttggt ctgacagtta   7680

ccaatgctta atcagtgagg cacctatctc agcgatctgt ctatttcgtt catccatagt   7740

tgcctgactc cccgtcgtgt agataactac gatacgggag ggcttaccat ctggccccag   7800

tgctgcaatg ataccgcgag acccacgctc accggctcca gatttatcag caataaacca   7860

gccagccgga agggccgagc gcagaagtgg tcctgcaact ttatccgcct ccatccagtc   7920

tattaattgt tgccgggaag ctagagtaag tagttcgcca gttaatagtt tgcgcaacgt   7980

tgttgccatt gctacaggca tcgtggtgtc acgctcgtcg tttggtatgg cttcattcag   8040

ctccggttcc caacgatcaa ggcgagttac atgatccccc atgttgtgca aaaaagcggt   8100

tagctccttc ggtcctccga tcgttgtcag aagtaagttg gccgcagtgt tatcactcat   8160

ggttatggca gcactgcata attctcttac tgtcatgcca tccgtaagat gcttttctgt   8220

gactggtgag tactcaacca agtcattctg agaatagtgt atgcggcgac cgagttgctc   8280

ttgcccggcg tcaacacggg ataataccgc gccacatagc agaactttaa aagtgctcat   8340

cattggaaaa cgttcttcgg ggcgaaaact ctcaaggatc ttaccgctgt tgagatccag   8400

ttcgatgtaa cccactcgtg cacccaactg atcttcagca tcttttactt tcaccagcgt   8460

ttctgggtga gcaaaaacag gaaggcaaaa tgccgcaaaa aagggaataa gggcgacacg   8520

gaaatgttga atactcatac tcttcctttt tcaatattat tgaagcattt atcagggtta   8580

ttgtctcatg acattaacct ataaaaatag gcgt                               8614
```

<210> SEQ ID NO 6
<211> LENGTH: 61
<212> TYPE: PRT
<213> ORGANISM: Unknown
<220> FEATURE:
<223> OTHER INFORMATION: Description of Unknown Organism: coiled-coil presentation structure
<300> PUBLICATION INFORMATION:
<301> AUTHORS: Martin et al., -continued

```
<303> JOURNAL: EMBO J.
<304> VOLUME: 13
<305> ISSUE: 22
<306> PAGES: 5303-5309
<307> DATE: 1994

<400> SEQUENCE: 6

Met Gly Cys Ala Ala Leu Glu Ser Glu Val Ser Ala Leu Glu Ser Glu
  1               5                  10                  15

Val Ala Ser Leu Glu Ser Glu Val Ala Ala Leu Gly Arg Gly Asp Met
             20                  25                  30

Pro Leu Ala Ala Val Lys Ser Lys Leu Ser Ala Val Lys Ser Lys Leu
         35                  40                  45

Ala Ser Val Lys Ser Lys Leu Ala Ala Cys Gly Pro Pro
     50                  55                  60


<210> SEQ ID NO 7
<211> LENGTH: 70
<212> TYPE: PRT
<213> ORGANISM: Unknown
<220> FEATURE:
<223> OTHER INFORMATION: Description of Unknown Organism:  minibody
      presentation structure

<400> SEQUENCE: 7

Met Gly Arg Asn Ser Gln Ala Thr Ser Gly Phe Thr Phe Ser His Phe
  1               5                  10                  15

Tyr Met Glu Trp Val Arg Gly Gly Glu Tyr Ile Ala Ala Ser Arg His
             20                  25                  30

Lys His Asn Lys Tyr Thr Thr Glu Tyr Ser Ala Ser Val Lys Gly Arg
         35                  40                  45

Tyr Thr Ile Val Ser Arg Asp Thr Ser Gln Ser Ile Leu Tyr Leu Gln
     50                  55                  60

Lys Lys Lys Gly Pro Pro
 65                  70


<210> SEQ ID NO 8
<211> LENGTH: 7
<212> TYPE: PRT
<213> ORGANISM: Monkey virus
<300> PUBLICATION INFORMATION:
<301> AUTHORS: Kalderon,
<303> JOURNAL: Cell
<304> VOLUME: 39
<306> PAGES: 499-509
<307> DATE: 1984

<400> SEQUENCE: 8

Pro Lys Lys Lys Arg Lys Val
  1               5


<210> SEQ ID NO 9
<211> LENGTH: 6
<212> TYPE: PRT
<213> ORGANISM: Homo sapiens

<400> SEQUENCE: 9

Ala Arg Arg Arg Arg Pro
  1               5


<210> SEQ ID NO 10
<211> LENGTH: 10
<212> TYPE: PRT
<213> ORGANISM: Unknown
```

-continued

```
<220> FEATURE:
<223> OTHER INFORMATION: Description of Unknown Organism:  NLS
<300> PUBLICATION INFORMATION:
<301> AUTHORS: Ghosh et al.,
<303> JOURNAL: Cell
<304> VOLUME: 62
<306> PAGES: 1019-1019
<307> DATE: 1990

<400> SEQUENCE: 10

Glu Glu Val Gln Arg Lys Arg Gln Lys Leu
  1               5                  10


<210> SEQ ID NO 11
<211> LENGTH: 9
<212> TYPE: PRT
<213> ORGANISM: Unknown
<220> FEATURE:
<223> OTHER INFORMATION: Description of Unknown Organism:  NLS
<300> PUBLICATION INFORMATION:
<303> JOURNAL: J. Cell. Biochem.
<304> VOLUME: 55
<305> ISSUE: 1
<306> PAGES: 32-58
<307> DATE: 1994
<300> PUBLICATION INFORMATION:
<301> AUTHORS: Nolan et al.,
<303> JOURNAL: Cell
<304> VOLUME: 64
<306> PAGES: 961-961
<307> DATE: 1991

<400> SEQUENCE: 11

Glu Glu Lys Arg Lys Arg Thr Tyr Glu
  1               5


<210> SEQ ID NO 12
<211> LENGTH: 20
<212> TYPE: PRT
<213> ORGANISM: African clawed toad
<300> PUBLICATION INFORMATION:
<301> AUTHORS: Dingwall et al.,
<303> JOURNAL: J. Cell Biol.
<304> VOLUME: 30
<306> PAGES: 449-458
<307> DATE: 1988
<300> PUBLICATION INFORMATION:
<301> AUTHORS: Dingwall et al.,
<303> JOURNAL: Cell
<304> VOLUME: 30
<306> PAGES: 449-458
<307> DATE: 1982

<400> SEQUENCE: 12

Ala Val Lys Arg Pro Ala Ala Thr Lys Lys Ala Gly Gln Ala Lys Lys
  1               5                  10                  15

Lys Lys Leu Asp
             20


<210> SEQ ID NO 13
<211> LENGTH: 31
<212> TYPE: PRT
<213> ORGANISM: Unknown
<220> FEATURE:
<223> OTHER INFORMATION: Description of Unknown Organism:  signal
      sequence
<300> PUBLICATION INFORMATION:
<301> AUTHORS: Nakauchi et al.,
<303> JOURNAL: Proc. Natl. Acad. Sci. U.S.A.
<304> VOLUME: 82
<306> PAGES: 5126-5126
<307> DATE: 1985
```

```
<400> SEQUENCE: 13

Met Ala Ser Pro Leu Thr Arg Phe Leu Ser Leu Asn Leu Leu Leu Leu
  1               5                  10                  15

Gly Glu Ser Ile Leu Gly Ser Gly Glu Ala Lys Pro Gln Ala Pro
             20                  25                  30


<210> SEQ ID NO 14
<211> LENGTH: 21
<212> TYPE: PRT
<213> ORGANISM: Unknown
<220> FEATURE:
<223> OTHER INFORMATION: Description of Unknown Organism:  signal
      sequence
<300> PUBLICATION INFORMATION:
<301> AUTHORS: Staunton et al.,
<303> JOURNAL: Nature
<304> VOLUME: 339
<306> PAGES: 61-61
<307> DATE: 1989

<400> SEQUENCE: 14

Met Ser Ser Phe Gly Tyr Arg Thr Leu Thr Val Ala Leu Phe Thr Leu
  1               5                  10                  15

Ile Cys Cys Pro Gly
             20


<210> SEQ ID NO 15
<211> LENGTH: 51
<212> TYPE: PRT
<213> ORGANISM: Unknown
<220> FEATURE:
<223> OTHER INFORMATION: Description of Unknown Organism:  transmembrane
      domains
<300> PUBLICATION INFORMATION:
<301> AUTHORS: Nakauchi et al.,
<303> JOURNAL: Proc. Natl. Acad. Sci. U.S.A.
<304> VOLUME: 82
<306> PAGES: 5126-5126
<307> DATE: 1985

<400> SEQUENCE: 15

Pro Gln Arg Pro Glu Asp Cys Arg Pro Arg Gly Ser Val Lys Gly Thr
  1               5                  10                  15

Gly Leu Asp Phe Ala Cys Asp Ile Tyr Ile Trp Ala Pro Leu Ala Gly
             20                  25                  30

Ile Cys Val Ala Leu Leu Leu Ser Leu Ile Ile Thr Leu Ile Cys Tyr
         35                  40                  45

His Ser Arg
     50


<210> SEQ ID NO 16
<211> LENGTH: 33
<212> TYPE: PRT
<213> ORGANISM: Unknown
<220> FEATURE:
<223> OTHER INFORMATION: Description of Unknown Organism:  transmembrane
      domain
<300> PUBLICATION INFORMATION:
<301> AUTHORS: Staunton et al.,
<303> JOURNAL: Nature
<304> VOLUME: 339
<306> PAGES: 61-61
<307> DATE: 1989

<400> SEQUENCE: 16

Met Val Ile Ile Val Thr Val Val Ser Val Leu Leu Ser Leu Phe Val
```

-continued

```
  1               5                   10                  15

Thr Ser Val Leu Leu Cys Phe Ile Phe Gly Gln His Leu Arg Gln Gln
             20                  25                  30

Arg


<210> SEQ ID NO 17
<211> LENGTH: 37
<212> TYPE: PRT
<213> ORGANISM: Unknown
<220> FEATURE:
<223> OTHER INFORMATION: Description of Unknown Organism:  anchor site
<300> PUBLICATION INFORMATION:
<303> JOURNAL: Nature
<304> VOLUME: 333
<305> ISSUE: 6170
<306> PAGES: 269-272
<307> DATE: 1988
<300> PUBLICATION INFORMATION:
<303> JOURNAL: J. Biol. Chem.
<304> VOLUME: 266
<306> PAGES: 1250-1250
<307> DATE: 1991

<400> SEQUENCE: 17

Pro Asn Lys Gly Ser Gly Thr Thr Ser Gly Thr Thr Arg Leu Leu Ser
  1               5                  10                  15

Gly His Thr Cys Phe Thr Leu Thr Gly Leu Leu Gly Thr Leu Val Thr
             20                  25                  30

Met Gly Leu Leu Thr
         35


<210> SEQ ID NO 18
<211> LENGTH: 14
<212> TYPE: PRT
<213> ORGANISM: Unknown
<220> FEATURE:
<223> OTHER INFORMATION: Description of Unknown Organism:  myristylation
      sequence
<300> PUBLICATION INFORMATION:
<303> JOURNAL: Mol. Cell. Biol.
<304> VOLUME: 4
<305> ISSUE: 9
<306> PAGES: 1834-1834
<307> DATE: 1984
<300> PUBLICATION INFORMATION:
<303> JOURNAL: Science
<304> VOLUME: 262
<306> PAGES: 1019-1024
<307> DATE: 1993

<400> SEQUENCE: 18

Met Gly Ser Ser Lys Ser Lys Pro Lys Asp Pro Ser Gln Arg
  1               5                  10


<210> SEQ ID NO 19
<211> LENGTH: 26
<212> TYPE: PRT
<213> ORGANISM: Unknown
<220> FEATURE:
<223> OTHER INFORMATION: Description of Unknown Organism:  palmitolyated
      sequence
<300> PUBLICATION INFORMATION:
<303> JOURNAL: J. Biol. Chem.
<304> VOLUME: 269
<306> PAGES: 27791-27791
<307> DATE: 1994

<400> SEQUENCE: 19

Leu Leu Gln Arg Leu Phe Ser Arg Gln Asp Cys Cys Gly Asn Cys Ser
```

-continued

```
 1               5                  10                  15

Asp Ser Glu Glu Glu Leu Pro Thr Arg Leu
             20                  25


<210> SEQ ID NO 20
<211> LENGTH: 20
<212> TYPE: PRT
<213> ORGANISM: Unknown
<220> FEATURE:
<223> OTHER INFORMATION: Description of Unknown Organism:  palmitolyated
      sequence
<300> PUBLICATION INFORMATION:
<303> JOURNAL: J. Mol. Neurosci.
<304> VOLUME: 5
<305> ISSUE: 3
<306> PAGES: 207-207
<307> DATE: 1994

<400> SEQUENCE: 20

Lys Gln Phe Arg Asn Cys Met Leu Thr Ser Leu Cys Cys Gly Lys Asn
 1               5                  10                  15

Pro Leu Gly Asp
             20


<210> SEQ ID NO 21
<211> LENGTH: 19
<212> TYPE: PRT
<213> ORGANISM: Unknown
<220> FEATURE:
<223> OTHER INFORMATION: Description of Unknown Organism:  pamitolyated
      sequence
<300> PUBLICATION INFORMATION:
<303> JOURNAL: Nature
<304> VOLUME: 302
<306> PAGES: 33-33
<307> DATE: 1983

<400> SEQUENCE: 21

Leu Asn Pro Pro Asp Glu Ser Gly Pro Gly Cys Met Ser Cys Lys Cys
 1               5                  10                  15

Val Leu Ser


<210> SEQ ID NO 22
<211> LENGTH: 5
<212> TYPE: PRT
<213> ORGANISM: Unknown
<220> FEATURE:
<223> OTHER INFORMATION: Description of Unknown Organism:  lysosomal
      degradation sequence
<300> PUBLICATION INFORMATION:
<303> JOURNAL: Ann. N. Y. Acad. Sci.
<304> VOLUME: 674
<306> PAGES: 58-58
<307> DATE: 1992

<400> SEQUENCE: 22

Lys Phe Glu Arg Gln
 1               5


<210> SEQ ID NO 23
<211> LENGTH: 36
<212> TYPE: PRT
<213> ORGANISM: Unknown
<220> FEATURE:
<223> OTHER INFORMATION: Description of Unknown Organism:  lysosomal
      membrane sequence
<300> PUBLICATION INFORMATION:
<303> JOURNAL: Cell. Mol. Biol. Res.
<304> VOLUME: 41
```

-continued

<306> PAGES: 405-405
<307> DATE: 1995

<400> SEQUENCE: 23

```
Met Leu Ile Pro Ile Ala Gly Phe Phe Ala Leu Ala Gly Leu Val Leu
  1               5                  10                  15

Ile Val Leu Ile Ala Tyr Leu Ile Gly Arg Lys Arg Ser His Ala Gly
             20                  25                  30

Tyr Gln Thr Ile
         35
```

<210> SEQ ID NO 24
<211> LENGTH: 35
<212> TYPE: PRT
<213> ORGANISM: Unknown
<220> FEATURE:
<223> OTHER INFORMATION: Description of Unknown Organism: lysosomal membrane sequence
<300> PUBLICATION INFORMATION:
<303> JOURNAL: Biochem. Biophys. Res. Commun.
<304> VOLUME: 205
<306> PAGES: 1-5
<307> DATE: 1994

<400> SEQUENCE: 24

```
Leu Val Pro Ile Ala Val Gly Ala Ala Leu Ala Gly Val Leu Ile Leu
  1               5                  10                  15

Val Leu Leu Ala Tyr Phe Ile Gly Leu Lys His His His Ala Gly Tyr
             20                  25                  30

Glu Gln Phe
         35
```

<210> SEQ ID NO 25
<211> LENGTH: 27
<212> TYPE: PRT
<213> ORGANISM: Unknown
<220> FEATURE:
<223> OTHER INFORMATION: Description of Unknown Organism: mitrochondrial localization sequence
<300> PUBLICATION INFORMATION:
<303> JOURNAL: Eur. J. Biochem.
<304> VOLUME: 165
<306> PAGES: 1-6
<307> DATE: 1987

<400> SEQUENCE: 25

```
Met Leu Arg Thr Ser Ser Leu Phe Thr Arg Arg Val Gln Pro Ser Leu
  1               5                  10                  15

Phe Ser Arg Asn Ile Leu Arg Leu Gln Ser Thr
             20                  25
```

<210> SEQ ID NO 26
<211> LENGTH: 25
<212> TYPE: PRT
<213> ORGANISM: Unknown
<220> FEATURE:
<223> OTHER INFORMATION: Description of Unknown Organism: mictrochondrial localization sequence
<300> PUBLICATION INFORMATION:
<303> JOURNAL: Eur. J. Biochem.
<304> VOLUME: 165
<306> PAGES: 1-6
<307> DATE: 1987

<400> SEQUENCE: 26

```
Met Leu Ser Leu Arg Gln Ser Ile Arg Phe Phe Lys Pro Ala Thr Arg
  1               5                  10                  15
```

```
Thr Leu Cys Ser Ser Arg Tyr Leu Leu
            20                  25


<210> SEQ ID NO 27
<211> LENGTH: 64
<212> TYPE: PRT
<213> ORGANISM: Unknown
<220> FEATURE:
<223> OTHER INFORMATION: Description of Unknown Organism:
      mitrochondrial localization sequence
<300> PUBLICATION INFORMATION:
<303> JOURNAL: Eur. J. Biochem.
<304> VOLUME: 165
<306> PAGES: 1-6
<307> DATE: 1987

<400> SEQUENCE: 27

Met Phe Ser Met Leu Ser Lys Arg Trp Ala Gln Arg Thr Leu Ser Lys
  1               5                  10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60


<210> SEQ ID NO 28
<211> LENGTH: 41
<212> TYPE: PRT
<213> ORGANISM: Unknown
<220> FEATURE:
<223> OTHER INFORMATION: Description of Unknown Organism:
      mitrochondrial localization sequence
<300> PUBLICATION INFORMATION:
<303> JOURNAL: Eur. J. Biochem.
<304> VOLUME: 165
<306> PAGES: 1-6
<307> DATE: 1987

<400> SEQUENCE: 28

Met Lys Ser Phe Ile Thr Arg Asn Lys Thr Ala Ile Leu Ala Thr Val
  1               5                  10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40


<210> SEQ ID NO 29
<211> LENGTH: 4
<212> TYPE: PRT
<213> ORGANISM: Unknown
<220> FEATURE:
<223> OTHER INFORMATION: Description of Unknown Organism:  endoplasmic
      reticulum sequence
<300> PUBLICATION INFORMATION:
<303> JOURNAL: Royal Society London Transactions B
<304> VOLUME: B
<306> PAGES: 1-10
<307> DATE: 1992

<400> SEQUENCE: 29

Lys Asp Glu Leu
  1


<210> SEQ ID NO 30
<211> LENGTH: 15
```

<212> TYPE: PRT
<213> ORGANISM: Unknown
<220> FEATURE:
<223> OTHER INFORMATION: Description of Unknown Organism: adenovirus
<300> PUBLICATION INFORMATION:
<303> JOURNAL: EMBO J.
<304> VOLUME: 9
<306> PAGES: 3153-3153
<307> DATE: 1990

<400> SEQUENCE: 30

Leu Tyr Leu Ser Arg Arg Ser Phe Ile Asp Glu Lys Lys Met Pro
1 5 10 15

<210> SEQ ID NO 31
<211> LENGTH: 19
<212> TYPE: PRT
<213> ORGANISM: Unknown
<220> FEATURE:
<223> OTHER INFORMATION: Description of Unknown Organism: farnesylation sequence
<300> PUBLICATION INFORMATION:
<303> JOURNAL: Nature
<304> VOLUME: 302
<306> PAGES: 33-33
<307> DATE: 1983

<400> SEQUENCE: 31

Leu Asn Pro Pro Asp Glu Ser Gly Pro Gly Cys Met Ser Cys Lys Cys
1 5 10 15

Val Leu Ser

<210> SEQ ID NO 32
<211> LENGTH: 3
<212> TYPE: PRT
<213> ORGANISM: Unknown
<220> FEATURE:
<223> OTHER INFORMATION: Description of Unknown Organism: peroxisome matrix sequence
<300> PUBLICATION INFORMATION:
<303> JOURNAL: Proc. Natl. Acad. Sci. U.S.A.
<304> VOLUME: 4
<306> PAGES: 3264-3264
<307> DATE: 1987

<400> SEQUENCE: 32

Ser Lys Leu
1

<210> SEQ ID NO 33
<211> LENGTH: 15
<212> TYPE: PRT
<213> ORGANISM: Unknown
<220> FEATURE:
<223> OTHER INFORMATION: Description of Unknown Organism: geranylgeranylation sequence
<300> PUBLICATION INFORMATION:
<303> JOURNAL: Proc. Natl. Acad. Sci. U.S.A.
<304> VOLUME: 91
<306> PAGES: 11963-11963
<307> DATE: 1994

<400> SEQUENCE: 33

Leu Thr Glu Pro Thr Gln Pro Thr Arg Asn Gln Cys Cys Ser Asn
1 5 10 15

<210> SEQ ID NO 34
<211> LENGTH: 9
<212> TYPE: PRT
<213> ORGANISM: Unknown

```
<220> FEATURE:
<223> OTHER INFORMATION: Description of Unknown Organism:  destruction
      sequence
<300> PUBLICATION INFORMATION:
<303> JOURNAL: EMBO J.
<304> VOLUME: 1
<306> PAGES: 3053-3053
<307> DATE: 1996

<400> SEQUENCE: 34

Arg Thr Ala Leu Gly Asp Ile Gly Asn
  1               5


<210> SEQ ID NO 35
<211> LENGTH: 20
<212> TYPE: PRT
<213> ORGANISM: Unknown
<220> FEATURE:
<223> OTHER INFORMATION: Description of Unknown Organism:  secretory
      sequence
<300> PUBLICATION INFORMATION:
<303> JOURNAL: J. Immunol.
<304> VOLUME: 155
<306> PAGES: 3946-3946
<307> DATE: 1995

<400> SEQUENCE: 35

Met Tyr Arg Met Gln Leu Leu Ser Cys Ile Ala Leu Ser Leu Ala Leu
  1               5                  10                  15

Val Thr Asn Ser
             20


<210> SEQ ID NO 36
<211> LENGTH: 29
<212> TYPE: PRT
<213> ORGANISM: Unknown
<220> FEATURE:
<223> OTHER INFORMATION: Description of Unknown Organism:  secretory
      sequence
<300> PUBLICATION INFORMATION:
<303> JOURNAL: Nucleic Acids Res.
<304> VOLUME: 7
<306> PAGES: 30-30
<307> DATE: 1979

<400> SEQUENCE: 36

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr
             20                  25


<210> SEQ ID NO 37
<211> LENGTH: 27
<212> TYPE: PRT
<213> ORGANISM: Unknown
<220> FEATURE:
<223> OTHER INFORMATION: Description of Unknown Organism:  secretory
      sequence
<300> PUBLICATION INFORMATION:
<303> JOURNAL: Nature
<304> VOLUME: 284
<306> PAGES: 26-26
<307> DATE: 1980

<400> SEQUENCE: 37

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn
             20                  25
```

```
<210> SEQ ID NO 38
<211> LENGTH: 18
<212> TYPE: PRT
<213> ORGANISM: Unknown
<220> FEATURE:
<223> OTHER INFORMATION: Description of Unknown Organism:  secretory
      sequence
<300> PUBLICATION INFORMATION:
<303> JOURNAL: Proc. Natl. Acad. Sci. U.S.A.
<304> VOLUME: 80
<306> PAGES: 3563-3563

<400> SEQUENCE: 38

Met Lys Ala Lys Leu Leu Val Leu Leu Tyr Ala Phe Val Ala Gly Asp
  1               5                  10                  15

Gln Ile


<210> SEQ ID NO 39
<211> LENGTH: 24
<212> TYPE: PRT
<213> ORGANISM: Unknown
<220> FEATURE:
<223> OTHER INFORMATION: Description of Unknown Organism:  secretory
      signal sequence

<400> SEQUENCE: 39

Met Gly Leu Thr Ser Gln Leu Leu Pro Pro Leu Phe Phe Leu Leu Ala
  1               5                  10                  15

Cys Ala Gly Asn Phe Val His Gly
             20


<210> SEQ ID NO 40
<211> LENGTH: 7
<212> TYPE: PRT
<213> ORGANISM: Unknown
<220> FEATURE:
<223> OTHER INFORMATION: Description of Unknown Organism:  stability
      sequence
<220> FEATURE:
<221> NAME/KEY: UNSURE
<222> LOCATION: (3)..(4)
<223> OTHER INFORMATION: The amino acid at position 3 is any amino acid.

<400> SEQUENCE: 40

Met Gly Xaa Gly Gly Pro Pro
  1               5


<210> SEQ ID NO 41
<211> LENGTH: 2
<212> TYPE: PRT
<213> ORGANISM: Artificial Sequence
<220> FEATURE:
<223> OTHER INFORMATION: Description of Artificial Sequence:  linker
      consensus

<400> SEQUENCE: 41

Gly Ser
  1


<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:  linkder
      consensus
```

-continued

```
<400> SEQUENCE: 42

Gly Ser Gly Gly Ser
  1             5


<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:  linker
      consensus

<400> SEQUENCE: 43

Gly Gly Gly Ser
  1
```